United States Patent [19]

Pacala et al.

[11] Patent Number: 5,980,545
[45] Date of Patent: *Nov. 9, 1999

[54] CORING DEVICE AND METHOD

[75] Inventors: Thomas J. Pacala, Palm Desert, Calif.;
James Correia, Shelton; Oleg Shikhman, Fairfield, both of Conn.

[73] Assignee: United States Surgical Corporation, Norwalk, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/650,485

[22] Filed: May 13, 1996

[51] Int. Cl.$^6$ .................................................. A61B 17/00
[52] U.S. Cl. ............................ 606/170; 606/171; 604/22
[58] Field of Search .................................. 606/159, 166, 606/167, 170, 171, 176, 179, 180, 184; 128/753–755; 604/22

[56] References Cited

U.S. PATENT DOCUMENTS

| | | |
|---|---|---|
| 1,867,624 | 7/1932 | Hoffman . |
| 2,710,000 | 6/1955 | Cromer et al. ............................ 128/755 |
| 2,730,101 | 1/1956 | Hoffman . |
| 2,816,552 | 12/1957 | Hoffman . |
| 2,818,852 | 1/1958 | Kugler . |

(List continued on next page.)

FOREIGN PATENT DOCUMENTS

| | | |
|---|---|---|
| 0196519 | 3/1986 | European Pat. Off. . |
| 0429390 | 11/1990 | European Pat. Off. . |
| 0481684 | 10/1991 | European Pat. Off. . |
| 0553576 | 1/1992 | European Pat. Off. . |
| 0515867 | 12/1992 | European Pat. Off. . |
| 0669107 | 2/1995 | European Pat. Off. . |
| 0737486 | 10/1996 | European Pat. Off. . |
| 0738518 | 10/1996 | European Pat. Off. . |
| 2585233 | 7/1985 | France . |
| 2625429 | 7/1989 | France . |
| 1922584 | 5/1969 | Germany . |

(List continued on next page.)

OTHER PUBLICATIONS

Jeevanandam V., Auteri JS, oz MC, Watkins J., Rose EA, Smith CR, Myocardial Revascularization By Laser–Induced Channels, Surg Forum, 41:225–227, 1990.

Khazei AH, Kime WP, Papadopoulos C, Cowley RA, Myocardial Canalization: A New Method of Myocardial Revascularization, Ann. Thor. Surg., 6:163–171, 1968.

Kuzela L., Muller GE, Experimental Evaluation of Direct Transventricular Revascularization, J. Thorac. Cardiovascular Surg., 57:770–773, 1969.

Landreneau, R., Nawarawong W., Laughlin H., Ripperger J., Brown O., McDaniel W., McKown D., Curtis J., Direct $CO_2$ Laser "Revascularization" of the Myocardium, Lasers Surg. Med., 11:35–42, 1991.

Eliseenko VI, Skobelkin OK, Brekhov EI, Zradovsky SF, Morphological Study of Myocardial Revascularization By Laser, Bulletin Exp. Biol. Med., 12:737–739,1984.

Frazier OH, Cooley DA, Kadipasaoglu KA, Pehlivanoglu S., Lindenmeir M., Barasch E., Congler JL, Wilansky S., Moore WH, Myocardial Revascularization With Laser: Preliminary Findings. Circulation, vol. 92, No. 9:11–58–65, 1995.

(List continued on next page.)

*Primary Examiner*—Michael Buiz
*Assistant Examiner*—William W. Lewis

[57] ABSTRACT

A coring device for coring body tissue to define reproducible patent channels in the body tissue is provided. The coring device utilizes a coring member that is rotatable and linearly advanceable at coordinated predetermined rates to core body tissue. The device can include a suction assembly suitable for use during biopsy procedures and a cautery assembly to cauterize the cored body tissue. The coring member can also be oscillated along its longitudinal axis to effect cauterization and/or coring. The coring device is particularly suited for Transmyocardial Revascularization (TMR).

37 Claims, 19 Drawing Sheets

U.S. PATENT DOCUMENTS

| | | |
|---|---|---|
| 3,477,423 | 11/1969 | Griffith . |
| 3,692,020 | 9/1972 | Schied . |
| 3,989,033 | 11/1976 | Halpern et al. . |
| 4,461,305 | 7/1984 | Cibley . |
| 4,667,684 | 5/1987 | Leigh . |
| 4,776,346 | 10/1988 | Beraha et al. . |
| 4,926,877 | 5/1990 | Bookwalter . |
| 4,940,061 | 7/1990 | Terwilliger et al. . |
| 5,036,860 | 8/1991 | Leigh et al. . |
| 5,201,756 | 4/1993 | Horzewski et al. . |
| 5,488,958 | 2/1996 | Topel et al. .............................. 606/184 |
| 5,511,556 | 4/1996 | DeSantis . |
| 5,651,781 | 7/1997 | Grace ...................................... 606/170 |

FOREIGN PATENT DOCUMENTS

| | | |
|---|---|---|
| 56-61211 | 5/1981 | Japan . |
| 0483829 | 4/1969 | Switzerland . |
| 0534505 | 6/1970 | Switzerland . |
| 91/08707 | 6/1991 | WIPO . |
| WO9307819 | 4/1993 | WIPO . |
| WO9314711 | 8/1993 | WIPO . |
| WO9315672 | 8/1993 | WIPO . |
| WO9315676 | 8/1993 | WIPO . |
| WO9315677 | 8/1993 | WIPO . |
| WO9320767 | 10/1993 | WIPO . |
| WO9320768 | 10/1993 | WIPO . |
| WO9401374 | 1/1994 | WIPO . |
| WO9402077 | 2/1994 | WIPO . |
| WO9410922 | 5/1994 | WIPO . |
| WO9410923 | 5/1994 | WIPO . |
| WO9414383 | 7/1994 | WIPO . |
| WO9426184 | 11/1994 | WIPO . |
| WO9505212 | 2/1995 | WIPO . |
| WO9515724 | 6/1995 | WIPO . |
| WO9635469 | 11/1996 | WIPO . |
| WO9639962 | 12/1996 | WIPO . |
| WO9639964 | 12/1996 | WIPO . |
| WO9639965 | 12/1996 | WIPO . |
| WO9707735 | 3/1997 | WIPO . |
| WO9713468 | 4/1997 | WIPO . |
| WO9718768 | 5/1997 | WIPO . |
| WO9725101 | 7/1997 | WIPO . |

OTHER PUBLICATIONS

Goda T., Wierzbicki Z., Gaston A., Leandri J., Vouron J., Loisance D., Myocardial Revascularization By $CO_2$ Laser, Eur. Surg. Res., 19:113–117, 1987.

Goldman A., Greenstone SM, Preuss FS, Strauss SH, Chang ES., Experimental Methods For Producing A Collateral Circulation To The Heart Directly From The Left Ventricle, J. Thorac Surg. 31:364–374, 1956.

Hardy RI, Bove, KE, James FW, Kaplan S., Goldman L., A Histological Study of Laser–Induced Transmyocardial Chanels, Lasers Surg. Med., 6:563–573, 1987.

Hardy RI, James FW, Millard RW, Kaplan S., Regional Myocardial Blood Flow and Cardiac Mechanics in Dog Hearts With $CO_2$ Laser–Induced Intramyocardial Revascularization, Basic Res. Cardial, 85:179–197, 1990.

Horvath KA, Smith WJ, Laurence RG, Schoen EJ, Appleyard RF, Cohn LH, Recovery And Viability of AN Acute Myocardial Infarct After Transmyocardial Laser Revascularization.; JAAC., 25:258–263, 1995.

Mirhoseni M., Cayton MM, Muckerheide M., Laser Revascularization of the Heart, SPIE/Lasers Surg. Med., 357, 1982.

Mirhoseini M., Cayton MM, Shelgikar S., Fisher JC, Clinical Report: Laser Myocardial Revascularization, Lasers Surg. Med., 6:459–461, 1986.

Mirhoseni M., Cayton MM, Shelgikar S., Transmyocardial Laser Revascularization, JAAC Abstracts. 1994.

Mirhoseini M., Fisher JC, Cayton MM, Myocardial Revascularization By Laser: A Clinical Report, Lasers Surg. Med., 3:241–245, 1983.

Mirhoseini M., Muckerheide M., Cayton MM, Transventricular Revascularization By Laser, Lasers Surg. Med., 2:187–198, 1982.

Mirhoseini M., Shelgikar S., Cayton MM, Transmyocardial Laser Revascularization: A Review, J. Clin. Laser Med. Surg., 11:15–19, 1993.

Mirhseini M., Shelgikar S., Cayton MM, Clinical and Histological Evaluation of Laser Myocardial Revascularization, J. Clin. Laser Med. Surg, pp. 73–78, 1990.

Mirhosini M., Shelgikar S., Cayton MM, New Concepts in Revascularization of the Myocardium, Ann. Thorac. Surg., vol. 45, No. 4:415–420, 1988.

Mirhoseini, M. Revascularization of the Myocardium With Laser, 2nd Henry Ford Hospital Int'l Symposium on Cardiac Surgery, Appleton–Century–Crofts, New York, pp. 595–597, 1977.

Anabtawi IN, Reigler HF, Ellison RG, Experimental Evaluation of Myocardial Tunnelization As A Method of Myocardial Revascularization, J. Thoracic Cardiovascular Surgery, 58:638–646, 1969.

Cooley DA, Frazier OH, Kadipasaoglu K., Pehlivanoglu S., Shannon RL, Angelini P., Transmyocardial Laser Revascularization: Anatomic Evidence of Long Term Channel Patency, Texas Heart Inst. Journal 21:220–224, 1994.

Crew JR, Transmyocardial Revascularization by $Co^2$ Laser, Surg. Tech. Intl., 1:236–238, 1991.

Okada M., Ikuta H., Shimizu H., Horii H., Nakamura K., Alternative Method of Myocardial Revascularization By Laser: Experimental and Clinical Study, Kobe J. Med Sci., 32:151–161, 1986.

Okada M., Shimizu H., Ikuta H., Nakamura K., A New Method of Myocardial Revascularization By Laser. Thorac Cardiovasc. Surg. 39:1–4, 1991.

Pifarre R., Jasuja ML, Lynch RD, Neville WE, Myocardial Revascularization By Transmyocardial Acupuncture: A Physiologic Impossibility, J. Thoracic Cardiovasc. Surg., vol. 58, No. 3:424–431, 1969.

Ping T., Liu XJ, Ming SQ, Ren SJ, Xun CX, Xing LH, Ying N., Long I., Experiment Study of $CO_2$ Laser Produce Myocardial Canal, Chinese J. Cardiol. 1990.

Sen PK, Daulatram J., Kinare SG, Udwadia TE, Parulkar GB, Further Studies In Multiple Transmyocardial Acupuncture As A Method of Myocardial Revascularization, Surgery, vol. 64, No. 5:861–870, 1968.

Sen PK, Udwadia TE, Kinare SG, Parulkar GB, Transmyocardial Acupuncture: A New Approach to Myocardial Revascularization, J. Thoracic Cardiovasc. Surg., vol. 50, No. 2:181–189, 1965, Sen PK, Studies in Myocardial Revascularization, Indian J. Med. Res., 57:415–433, 1969.

Vineberg A., The Formation of Artificial Thebesian Canals in the Wall of the Left Ventricle, Canad M A J, 69:158, 1953.

Vineberg AM, Baichwal KS, Myers J., Treatment of Acute Myocardial Infarction By Endocardial Resection, Surgery, 57:832, 1965.

Wakabayashi A., Little ST, Connolly JE, Myocardial Boring For the Ischemic Heart, Arch. Surg., 95:743, 1967.

Walter P., Hundeshagen H., Borst HG, Treatment of Acute Myocardial Infarction By Transmural Blook Supply From the Ventricular Cavity, Eur. Surg. Res. 3:130–138, 1971.

Wearn LT, Mettier SR, Klum TG, Zschiesche AM, The Nature of Vascular Communications Between Coronary Arteries and the Chambers of the Heart, Am Heart J., 9:143–164, 1933.

White M. Hershey JE, Multiple Transmyocardial Puncture Revascularization in Refractory Ventricular Fibrillation Due to Myocardial Ischemia., Ann. Thorac. Surg., vol. 6, No. 6:557–563, 1968.

Whittaker P., Kloner RA, Przyklenk K., Laser–Mediated Transmural Myocardial Channels Do Not Salvage Acutely Ischemic Myocardium. JACC., vol. 22, No. 1:302–309, 1993.

Whittaker P., Rakusan K., Kloner RA, Transmural Channels Can Protect Ischemic Tissue: Assessment of Long–term Myocardial Response to Laser–and–Needle–Made Channels, Circulation, vol. 93, No. I: 143–151, 1996.

Whittaker P., Zheng SM, Kloner RA, Chronic Response to Direct Myocardial Revascularization: A Preliminary Study, SPIE, vol. 1878:160–166, 1993.

Whittaker P., Zheng SM, Kloner RA, Beneficial Effects of Transmural Myocardial Channels: Chronic Response to Laser and Needle Treatment; AHA Abstracts, 66th Scientific Session, 1–435, 1993.

Yano O., Bielefeld MR, Jeevanandam V., Treat MR, Marboe CC, Spotnitz HM, Smith CR, Prevention of Acute Regional Ischemia With Endocardial Laser Channels, Ann. Thorac. Surg., 56:46–53, 1993.

Kohmoto T., Fisher PE, Gu A., Zhu SM, Yano OJ, Spotnitz HM, Smith CR, Burkhoff D., Does Blood Flow Through Holmium: YAG Transmyocardial Laser Channels?, Ann. Thorac. Surg., 61:861–868, 1996.

Lary BG, Effect of Endocardial Incisions on Myocardial Blood Flow, Arch. Surg, Chicago, 87:424–427, 1963.

Massimo C., Boffi L., Myocardial Revascularization By A New Method of Carrying Blood Directly From the Left Ventricular Cavity Into the Coronary Circulation, J. Thorac. Surg., 34:257–264, 1957.

Mirhoseini M. Cayton MM, Use of Cardioplegia For Laser Revascularization of Myocardium (abstr.), Lasers Surg. Med., 5:169,1985.

Mirhoseini M., Cayton MM, Revascularization of the Heart By Laser, J. Microsurg., 2:253–260, 1981.

A Histologic Study of Laser–Induced Transmyocardial Channels, Hardy et al., Lasers in Surgery and Medicine, vol. 6, No. 6, Alan R. Liss, Inc., New York (1987).

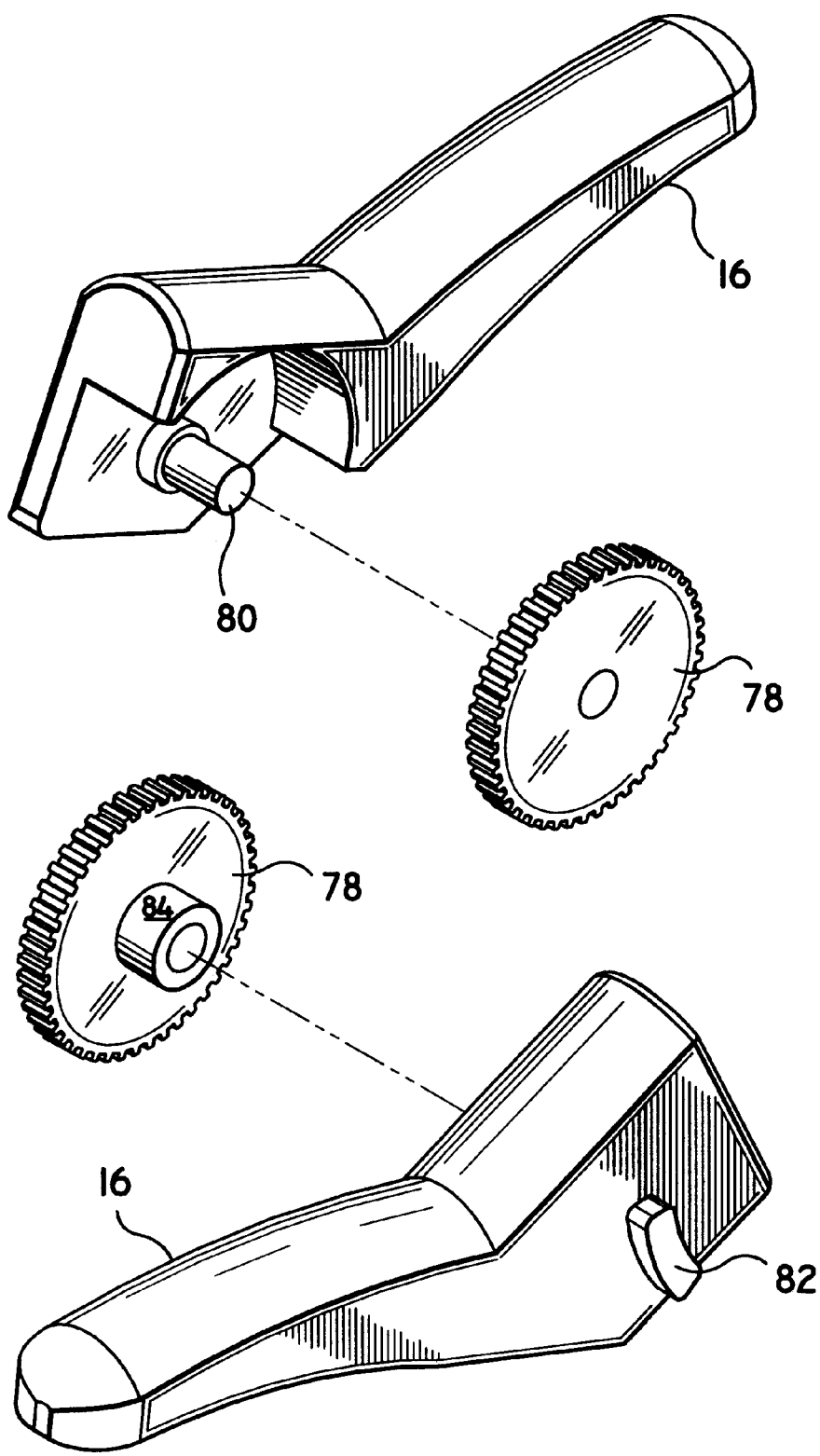

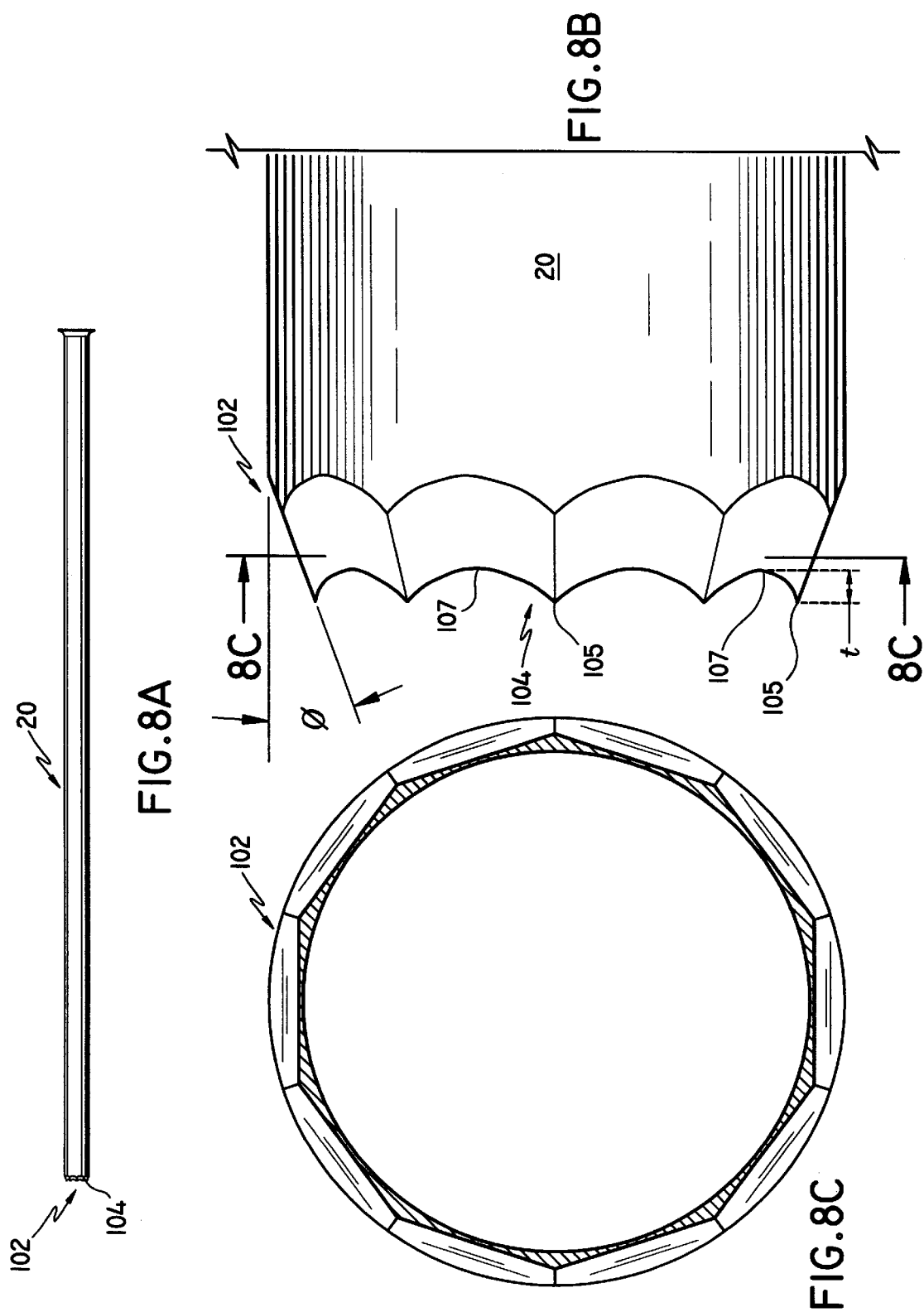

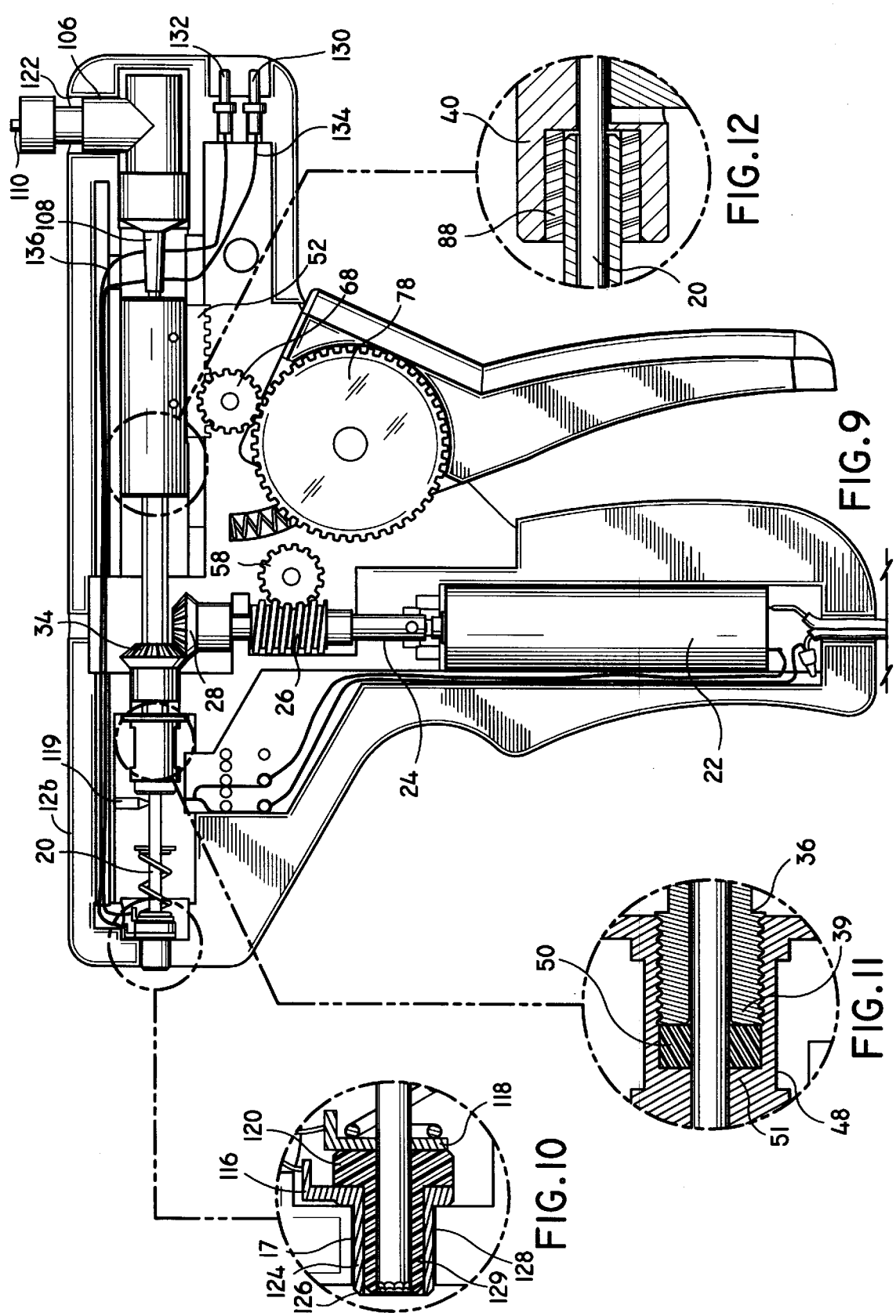

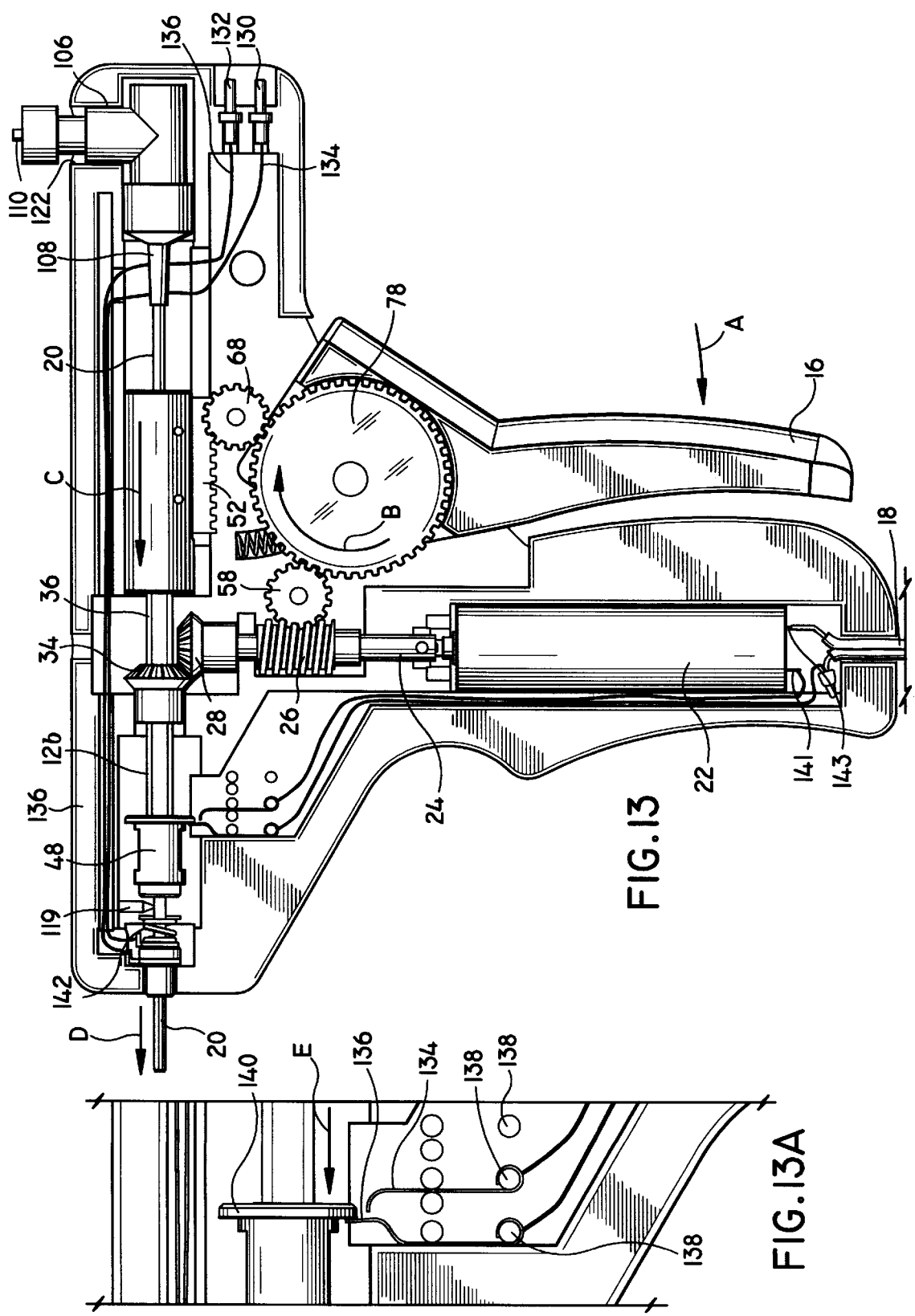

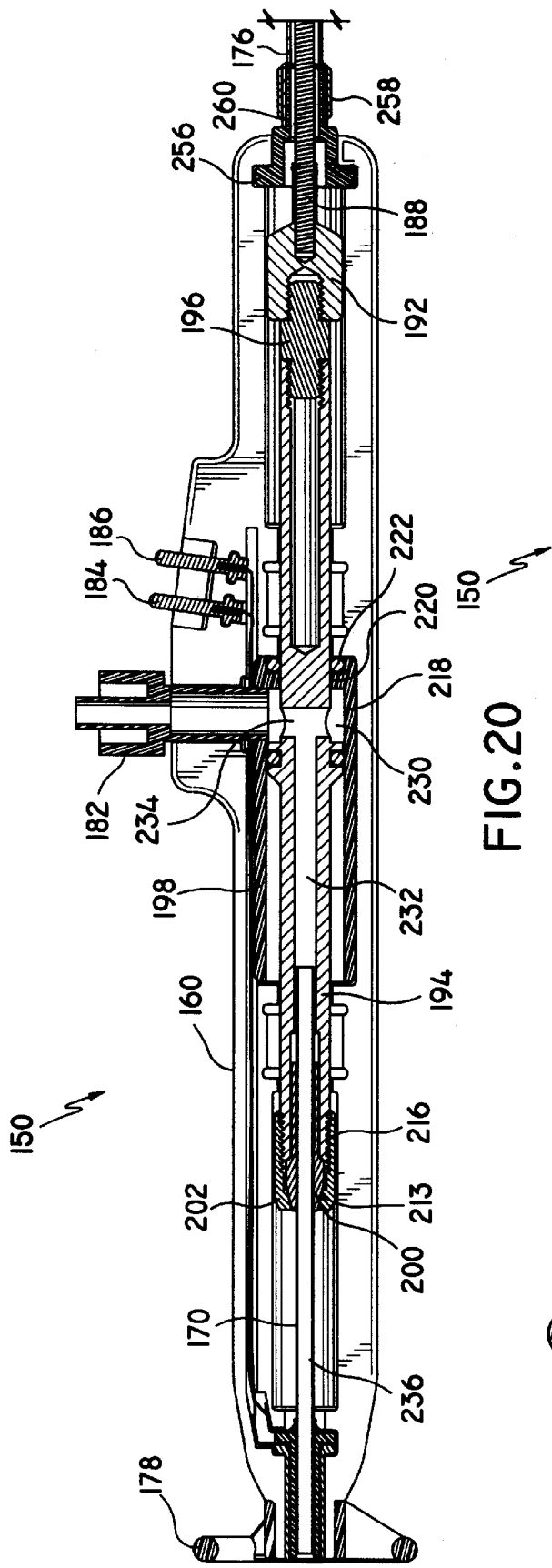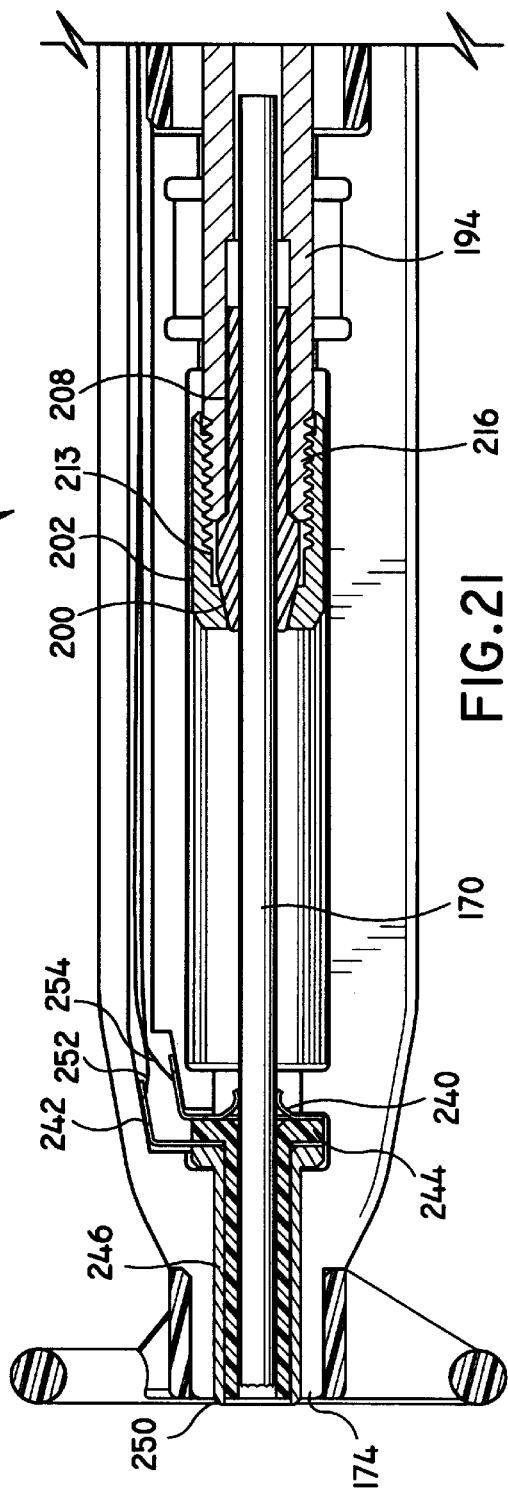

CORING DEVICE AND METHOD

BACKGROUND

1. Technical Field

The present disclosure relates generally to a coring device for surgical use. More specifically, the present disclosure relates to a coring device having an advanceable member operated at a coordinated speed to facilitate reproducible coring of body tissue. The coring device is particularly suited for use in performing transmyocardial revascularization (TMR).

2. Background of the Related Art

Mechanical coring devices suitable for use in surgical procedures such as biopsy retrieval, bone marrow retrieval, and similar procedures are well known. Typically, these coring devices include a tubular body having a sharpened end, and a cutting member. During coring procedures, the tubular body is manually advanced into body tissue such that a core of material is retrieved and retained within the tubular body. Thereafter, the cored tissue is removed for analysis.

One problem associated with these devices is that variations in the rate of advancement of the tubular body into the body tissue effect the size and shape of the cored tissue sample, e.g., a high rate of advancement can cause tearing of body tissue rather than precise coring of the tissue. Because of this, manual advancement makes it very difficult to retrieve good tissue samples of consistent size and shape required for biopsy. U.S. Pat. No. 4,461,305 issued to Cibley, addresses the problem of obtaining more consistent tissue sample sizes. Cibley discloses a biopsy device having a rotatable shaft with a cutting edge at its distal end. As the shaft is rotated, a trigger is compressed to manually advance the shaft into body tissue. Although Cibley improves upon the prior art, the performance of Cibley's device is directly related to the rate at which the shaft is manually advanced into the body tissue. Because the shaft is manually advanced, reproducible coring for the particular body tissue is difficult to achieve.

Mechanical devices have also been used in other surgical procedures. One such procedure is Transmyocardial Revascularization (TMR). In this procedure, surgical needles, biopsy needles, cannulas or similar instruments have been used to produce channels from the epicardium, through the myocardium and into the ventricle of the heart. It is believed that these channels facilitate delivery of blood directly from the ventrical to the oxygen starved areas of the heart. When performing a TMR procedure, 1 or more and typically dozens of channels are created in the heart. Because heart tissue has a soft, spongy texture that can be easily torn or deformed, it is difficult, if not impossible, to create consistent, reproducible channels by the aforementioned manual puncturing and coring techniques.

Accordingly, a need exists for an improved mechanical coring device that is easy to use, consistent and reliable when coring channels in body tissue.

SUMMARY

In accordance with the present disclosure, a coring device is provided that is capable of consistently coring channels of common size and shape in body tissue. The coring device can include a rotation assembly for rotating a coring member, and an advancement assembly for linearly advancing the coring member. An oscillator assembly can also be incorporated to assist in coring tissue. The rotation assembly and the advancement assembly are preferably driven to coordinate the rate of rotation of the coring member with the rate of linear advancement of the member. Both longitudinal and rotational reciprocation of the coring member can also be used to effect efficient coring. The coring device can be used to perform biopsy retrieval, bone marrow retrieval and other similar procedures, but is particularly suited to perform TMR.

In a first preferred embodiment of the disclosure, a drive assembly is supported within a housing of the coring device and includes a motor that is coupled to a rotatable rod having a bevel gear and a worm fixed thereto. The bevel gear is operably associated with the rotation assembly to rotate the coring member when the motor is operated. The worm is operably associated with the coring member such that the worm can be selectively coupled to drive a toothed rack to advance the coring member linearly. The rates of rotation and advancement of the coring member are coordinated to provide a reproducible cored channel in body tissue.

In another preferred embodiment, the driving assembly is incorporated into a dual-motion, independently programmable, control module that translates precise linear and rotary motion to a coring member via a flexible shaft. The device is preferably operated by a foot pedal which is operably connected to the control module to advance and rotate the coring member.

BRIEF DESCRIPTION OF THE DRAWINGS

Various preferred embodiments are described herein with reference to the drawings, wherein:

FIG. 6 is a front perspective view with parts separated of the movable handle and the actuation gear of the coring device shown in FIG. 1;

FIG. 7 is a rear perspective view with parts separated of the back side of the movable trigger and the actuation gear of the coring device shown in FIG. 1;

FIG. 8A is a side elevational view of a preferred coring member suitable for use with the coring devices shown in FIGS. 1 and 16;

FIG. 8B is an enlarged side elevational view of the distal end of the coring member shown in FIG. 8A.

FIG. 8C is an elevational view of the coring member taken along line 8C in FIG. 8B.

FIG. 9 is a side cross-sectional view of the coring device shown in FIG. 1;

FIG. 10 is an enlarged view of the indicated area of detail of FIG. 9;

FIG. 11 is an enlarged view of the indicated area of detail of FIG. 9;

FIG. 12 is an enlarged view of the indicated area of detail of FIG. 9;

FIG. 13 is a side cross-sectional view of the device shown in FIG. 1 with the movable trigger in position to actuate the advancement mechanism;

FIG. 13A is an enlarged partial side view of the coring device illustrating a stroke control assembly of the device shown in FIG. 1;

FIG. 20 is a side cross-sectional view of the coring device shown in FIG. 15;

FIG. 21 is an enlarged side cross-sectional view of the distal end of the coring device shown in FIG. 15;

FIG. 22 is a partial perspective view of the distal end of the coring device shown in FIG. 15 with a housing half-section removed;

DETAILED DESCRIPTION OF PREFERRED EMBODIMENTS

Figure 1:
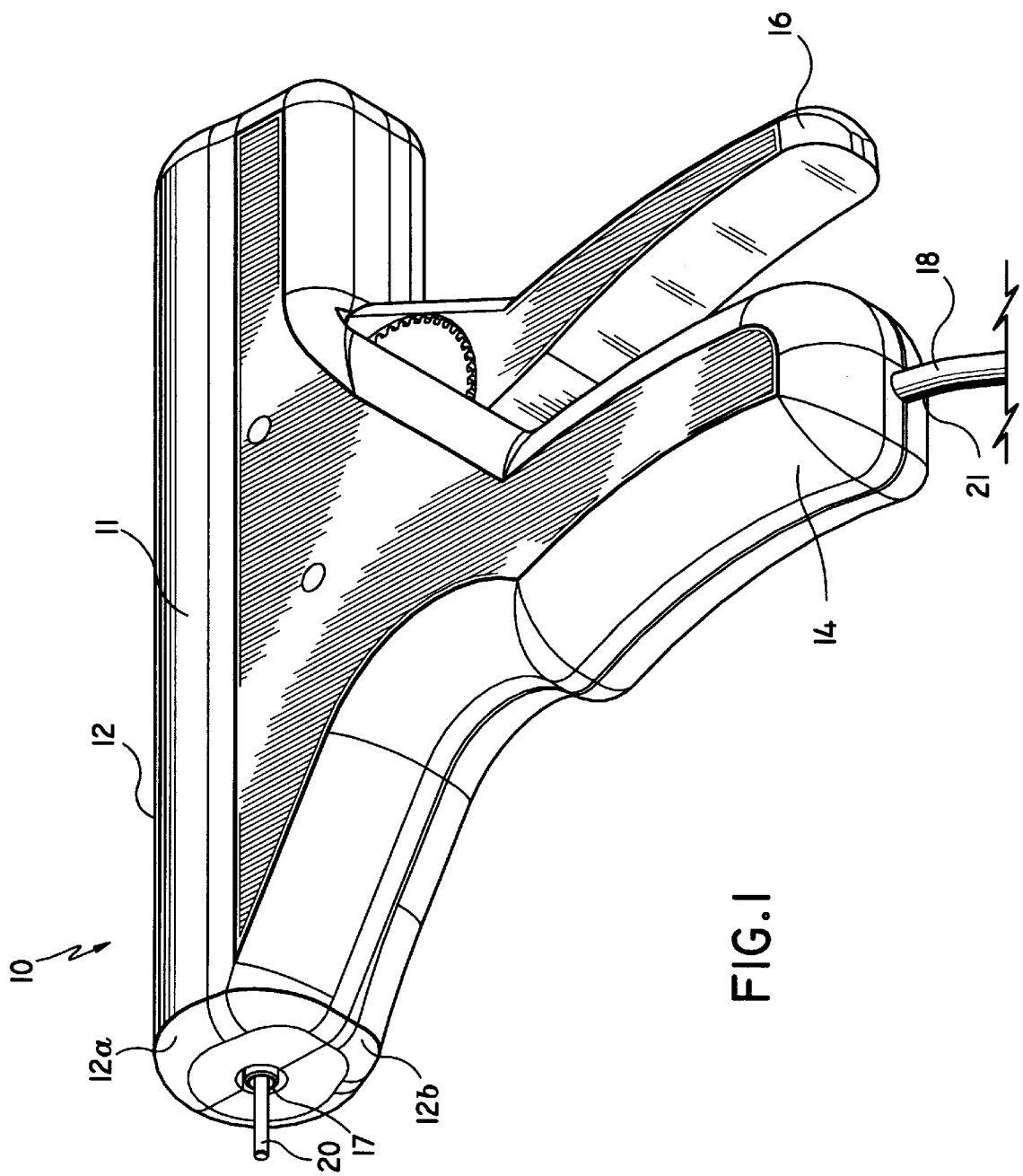
FIG. 1 is a perspective view of one embodiment of the coring device.

Preferred embodiments of the presently disclosed coring device will now be described in detail with reference to the drawings, in which like reference numerals designate identical or corresponding elements in each of the several views.

While the preferred embodiments of the coring device of the present disclosure are useful to perform biopsy retrieval, bone marrow retrieval, and other similar procedures, the presently disclosed coring devices are particularly suited to perform Transmyocardial Revascularization (TMR). The preferred embodiments of coring device will, therefore, be described in connection with their use in performing TMR.

Figure 2:
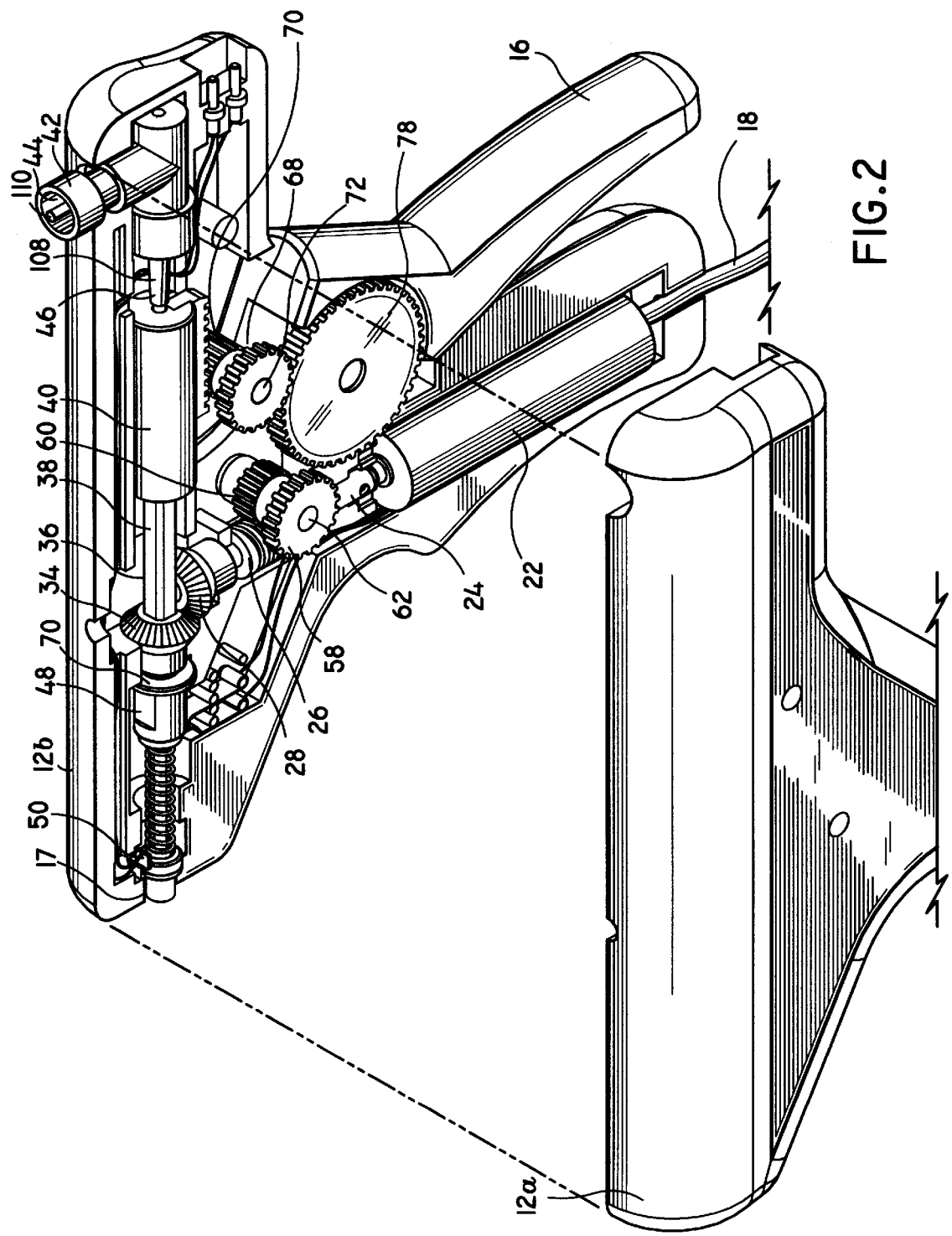
FIG. 2 is a perspective view of the coring device shown in FIG. 1 with housing half-sections separated.

One embodiment of the presently disclosed coring device will now be described with reference to FIGS. 1–14A. FIGS. 1 and 2 illustrate the coring device shown generally as 10. Briefly, coring device 10 includes a housing 12 formed from molded housing half-sections 12a and 12b. Housing 12 includes an elongated body portion 11 defining the longitudinal axis of device 10 and a stationary handle 14 projecting from elongated body portion 11. A movable trigger 16 is pivotably connected to housing 12 adjacent stationary handle 14 forming a pistol type grip. A first opening 17 dimensioned to receive coring member 20 is formed in one end of body portion 11. A second opening 21 formed in the free end of stationary handle 14 allows passage of power supply cable 18 into housing 12.

Figure 3:
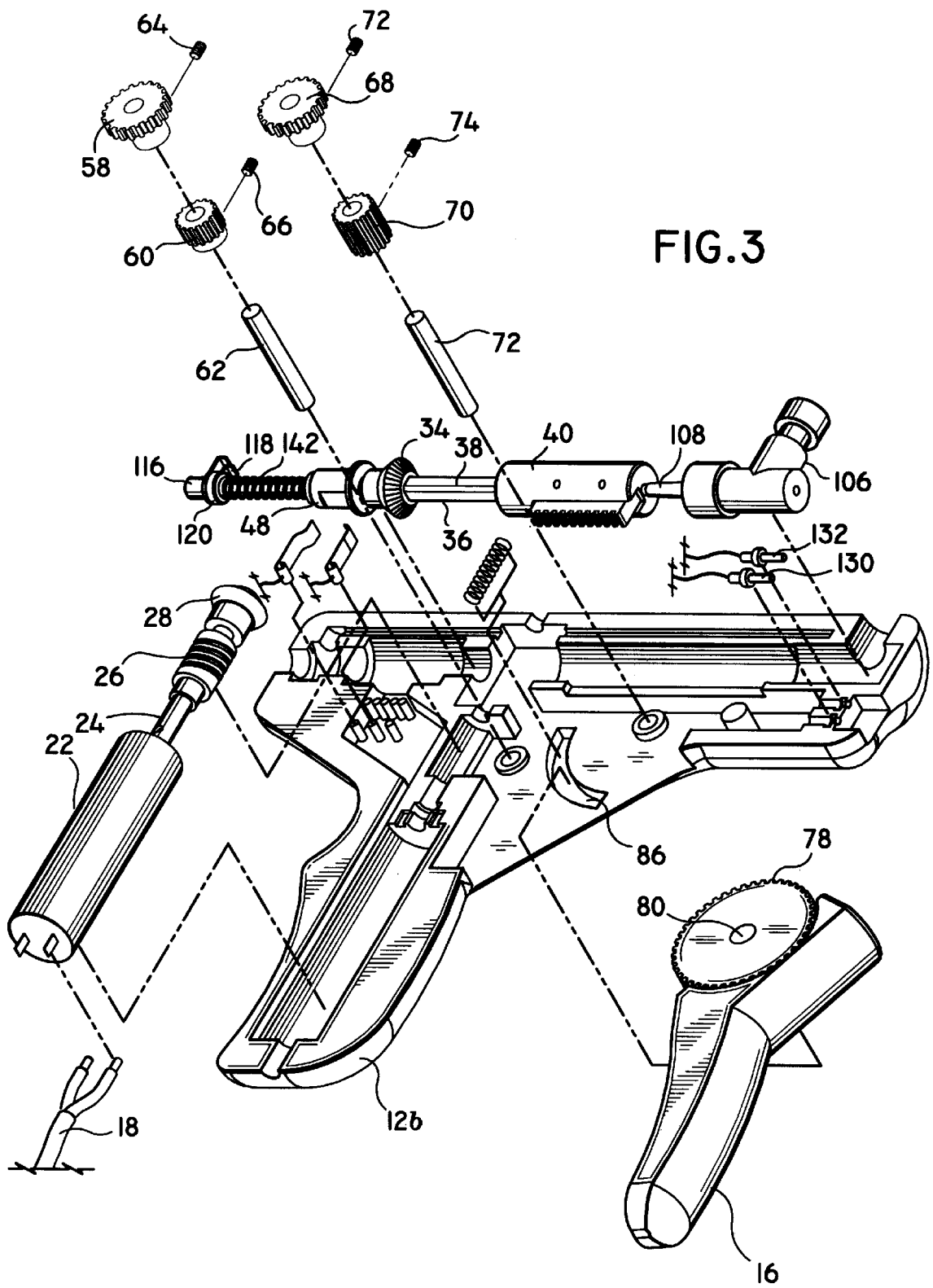
FIG. 3 is a perspective view with parts separated of the coring device shown in FIG. 1.
Figure 4:
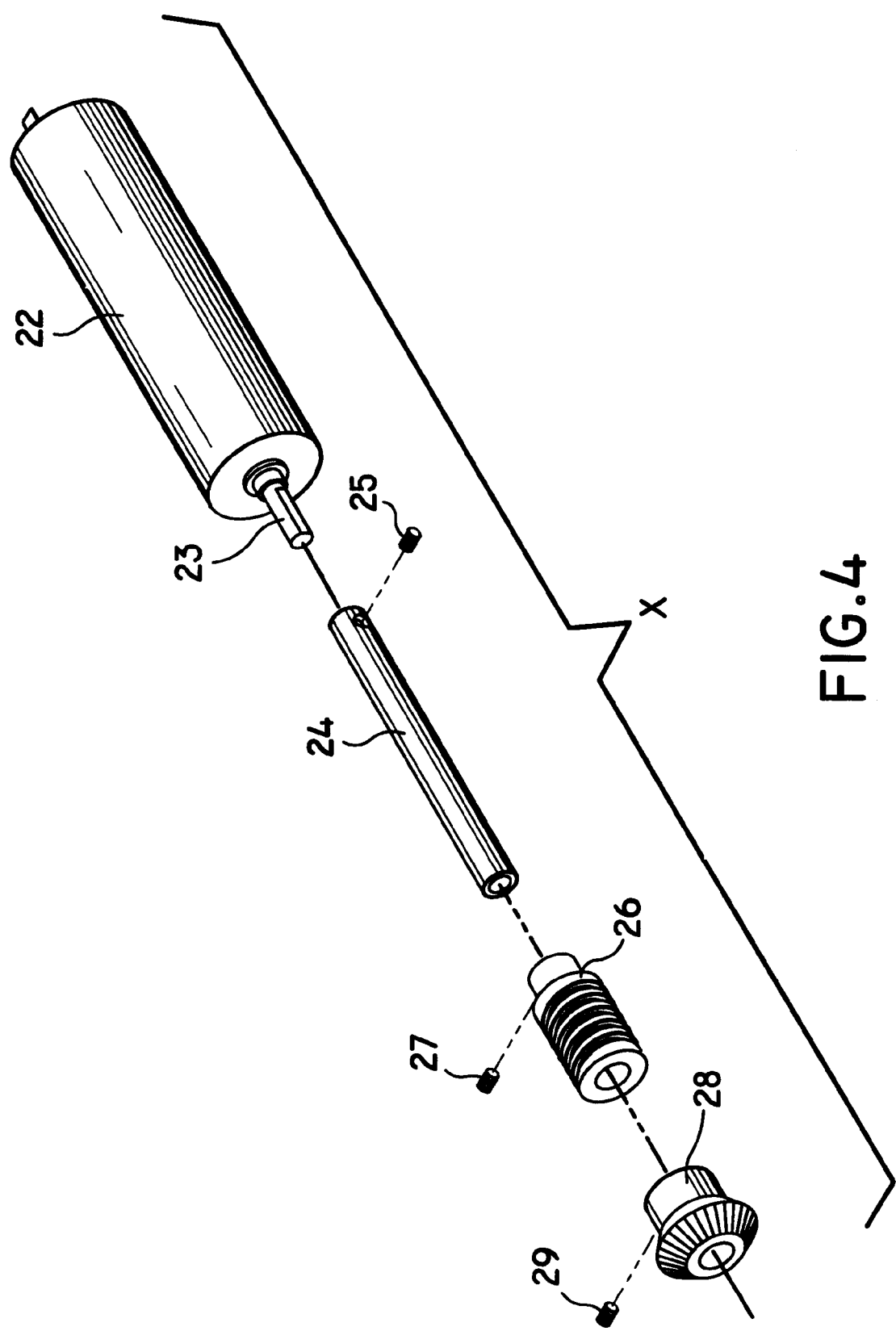
FIG. 4 is a perspective view with parts separated of the drive assembly of the coring device shown in FIG. 1.

FIGS. 2 and 3 illustrate the internal components of coring device 10 which will now be discussed in detail. Housing half-sections 12a and 12b are formed with internal recesses configured to properly align the internal components of the device with respect to each other and to restrict the movable components to a predetermined path of travel. Coring device 10 includes a member drive assembly, a member rotation assembly, and a member advancement assembly. FIG. 4 illustrates the member drive assembly "X" which includes a motor 22 which is adapted to be electrically connected to power supply cable 18. Motor 22 drives output shaft 23 which is coupled to a cylindrical shaft 24 by a locking screw 25. Rotation of output shaft 23 translates to rotation of cylindrical shaft 24. A worm 26 and a bevel gear 28 are slidably received and fastened about cylindrical shaft 24 by locking screws 27 and 29, respectively. Upon rotation of output shaft 23, cylindrical shaft 24 rotates causing worm 26 and bevel gear 28 to also rotate.

Figure 5:
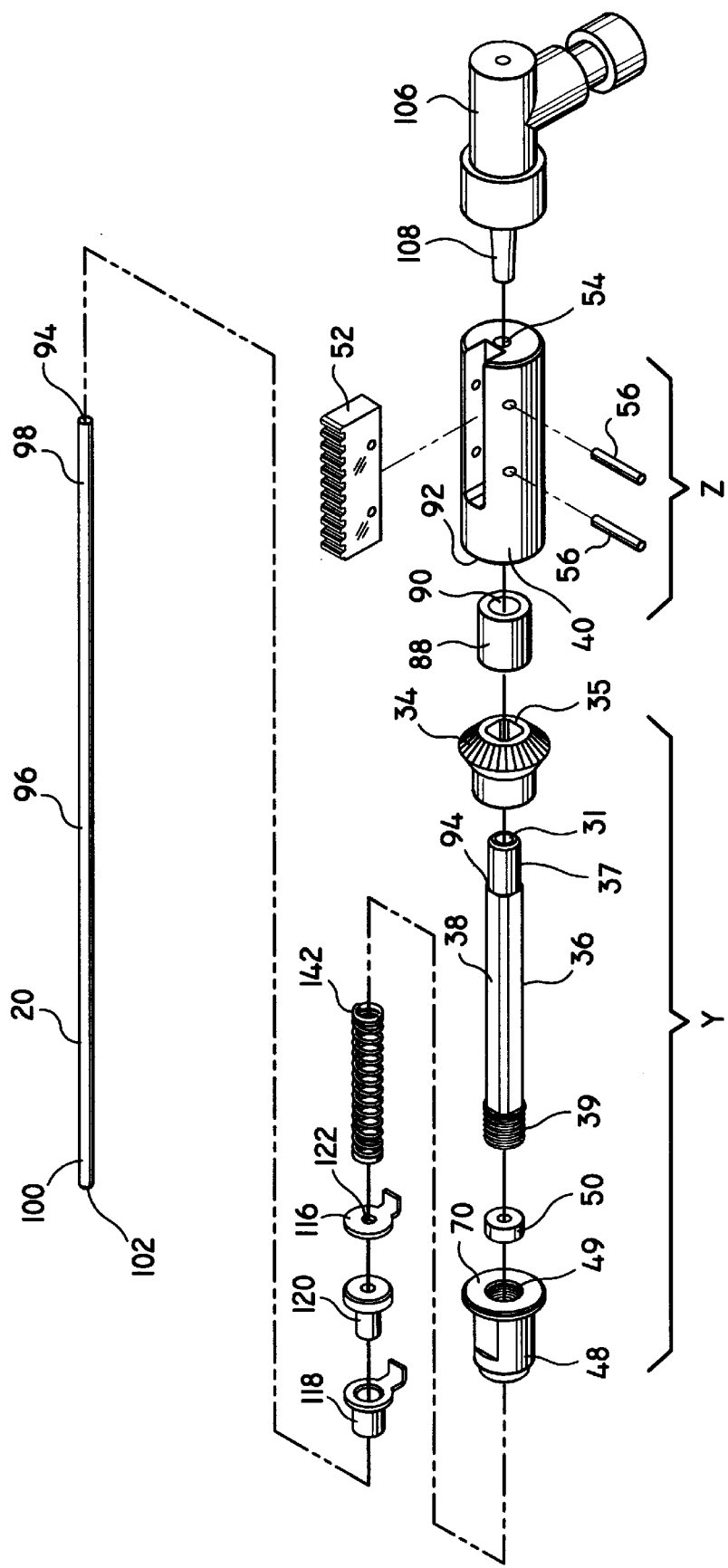
FIG. 5 is a perspective view with parts separated of the rotation assembly and advancement assembly of the coring device shown in FIG. 1.

Referring to FIG. 5, the member rotation assembly "Y" includes a bevel gear 34 having a rectangular bore 35 extending therethrough. A rod member 36 having a rectangular central portion 38 is positioned within rectangular bore 35 of bevel gear 34 such that rotation of bevel gear 34 causes corresponding rotation of rod member 36. Rod member 36 further includes a longitudinal throughbore 31 dimensioned to receive coring member 20, a threaded first end 39, and a cylindrical second end 37. Cylindrical second end 37 of rod member 36 interconnects rotation assembly "Y" and advancement assembly "Z", to be discussed in detail below.

A compression nut 48 having a threaded cylindrical bore 49 threadingly engages the first end 39 of rod member 36. A flexible annular washer 50 is positioned within cylindrical bore 49 between an inwardly extending flange 51 on the compression nut 48 and the threaded first end of rod member 36. See FIG. 11. Coring member 20 extends proximal to advancement mechanism "Z" through rod member 36 and compression nut 48 towards the distal end of body portion 11. As compression nut 48 is threaded onto rod member 36, flexible washer 50 is compressed and deformed into engagement with coring member 20 extending therethrough, thus securing coring member 20 to compression nut 48.

Bevel gear 28 of member drive assembly "X" engages bevel gear 34 of member rotation assembly "Y". Upon actuation of motor 22, bevel gear 28 is rotated, rotating bevel gear 34 and rod member 36. Since rod member 36 is threadingly fastened to compression nut 48, compression nut 48 is also rotated. Flexible washer 50 rotates with compression nut 48 and is frictionally engaged with coring member 20 to rotate coring member 20.

The member advancement assembly "Z" includes a cylindrical member 40 having a central throughbore 42 and a toothed rack 52. Cylindrical member 40 has a slot 54 configured to receive toothed rack 52 such that the teeth on toothed rack 52 extend outwardly from the outer periphery of cylindrical member 40. A pair of pins 56 may be used to lock toothed rack 52 within slot 54.

As shown in FIGS. 2 and 3, a first and a second gear set are positioned within the housing 12 of coring device 10. The first gear set includes gear 58 and worm gear 60 which are fixedly mounted on a common rotatable shaft 62 by locking screws 64 and 66, respectively. The second gear set includes gears 68 and 70 which are fixedly mounted on a common rotatable shaft 72 by locking screws 74 and 76. Shafts 62 and 72 are mounted for rotation between cylindrical recesses formed in housing half-sections 12a and 12b.

Worm gear 60 of the first gear set engages worm 26 of member drive assembly "X" such that rotation of worm 26 causes rotation of worm gear 60. Since gear 58 and worm gear 60 are secured to common shaft 62, rotation of worm gear 60 causes corresponding rotation of shaft 62 and gear 58. Gear 72 of the second gear set engages an actuation gear 78 which is rotatably mounted to movable trigger 16. Likewise, since gears 68 and 70 are secured to common shaft 72, rotation of gear 68 causes corresponding rotation of shaft 72 and gear 70.

FIGS. 6 and 7 illustrate movable trigger 16 and actuation gear 78. Movable trigger 16 has a shaft 80 and a guide projection 82. Actuation gear 78 includes a central hub 84 which is rotatably mounted on shaft 80. The guide projection 82 is slidably received within a semi-circular slot 86 formed housing half-section 12b (FIG. 3), and is retained therein by attachment of housing half-section 12a to housing half-section 12b. Actuation gear 78 is in continuous engagement with gear 68 of the second gear set. When movable trigger 16 is actuated to move guide projection 82 along slot 86, actuation gear 78 is moved to a position also engaging gear 58 of the first gear set.

As stated above, worm 26 of member drive assembly "X" engages worm gear 60 of the first gear set. Upon actuation of motor 22, worm 26 is rotated by shaft 24, causing worm gear 60 to rotate. Rotation of worm gear 60 results in corresponding rotation of shaft 62 and gear 58. When movable trigger 16 is acted upon to move actuation gear 78 into engagement with gear 58, actuation gear 78 is caused to rotate. Since actuation gear 78 is engaged with gear 68 of the second gear set, gear 68 is rotated causing rotation of shaft 72 and gear 70. Gear 70 engages toothed rack 52, such that rotation of gear 70 is translated to linear movement of rack 52 and cylindrical member 40.

Referring again to FIG. 5, a cylindrical bearing 88 having a central bore 90 dimensioned to be slidably received about cylindrical bearing surface 37 of rod member 36 is fitted within a cylindrical recess 93 formed in a first end 92 of cylindrical member 40. See FIG. 12. Bearing surface 37 is rotatable within central bore 90 to allow rod member 36 to rotate with respect to cylindrical member 40. Further, the first end 92 of cylindrical member 40 engages an outer peripheral face 94 of the rectangular central portion 38 of rod member 36, such that linear movement of cylindrical member 40 causes linear movement of rod member 36, compression nut 48, and coring member 20.

Coring member 20 includes an elongated tubular member 96 having a central throughbore 94. The tubular member 96 preferably extends through the central throughbores of cylindrical member 40, bearing 88, bevel gear 34, rod member 36, flexible washer 50, and compression nut 48. A first end 98 of tubular member 96 extends from throughbore 42 of cylindrical member 40. The second end 100 of tubular member 96 extends from a forward end of threaded throughbore 49 of compression nut 48 towards opening 17 in housing 12. The second end of the tubular member 96 includes a cutting edge 102 which can be in the form of a flattened or a beveled edge.

Preferably, as illustrated in FIGS. 8A–8C, the cutting edge 102 is in the form of a serrated annular edge 104. Cutting edge 102 is formed from a plurality of spaced serrations formed at an angle with respect to the longitudinal axis of coring member 20. Preferably the serrations are flat cuts (see FIG. 8C) but can also be contoured such as, for example, being concave or convex. As shown, the serrations have a tooth depth 't', which is defined by the longitudinal distance between the distal-most portion of the serration edge 105 and the proximal-most portion of the serration edge 107. The tooth depth 't' preferably ranges from about 0.05 mm to about 0.3 mm. The angle 'φ' at which the serrations are cut preferably ranges from about 5° to about 40° while the number of serrations 'n' preferably ranges from about 4 to about 20. FIG. 8A–8C depict 10 serrations (n=10) cut at an angle of 20°. The following table sets forth several examples of preferred coring member dimensions when the serration angle '100' is 20°.

| Number of Serrations | Member Diameter (mm) | Inner Member Diameter (mm) | Tooth Depth (mm) |
|---|---|---|---|
| 8 | 2.1 | 1.9 | 0.203 (0.0080") |
| 10 | 2.1 | 1.9 | 0.147 (0.0058") |
| 12 | 2.1 | 1.9 | 0.091 (0.0036") |
| 8 | 1.8 | 1.6 | 0.170 (0.0067") |
| 10 | 1.8 | 1.6 | 0.112 (0.0044") |
| 12 | 1.8 | 1.6 | 0.084 (0.0033") |
| 8 | 1.65 | 1.37 | 0.152 (0.0060") |
| 10 | 1.65 | 1.37 | 0.102 (0.0040") |
| 12 | 1.65 | 1.37 | 0.076 (0.0030") |
| 8 | 1.42 | 1.17 | 0.132 (0.0052") |
| 10 | 1.42 | 1.17 | 0.081 (0.0032") |
| 12 | 1.42 | 1.17 | 0.066 (0.0026") |

The coring member 20 can be advanced at a rate of between about 0.1 to about 50 mm/sec and simultaneously rotated at a rate of between about 1 to about 3000 rpm. Ideally, when coring body tissue, the coring member is advanced at a rate of between about 2 to about 4 mm/sec and simultaneously rotated at a rate of between about 100 to about 140 rpm. Coring has been accomplished in canine heart tissue where the coring member 20 was advanced at a rate of about 3 mm/sec and rotated at a rate of 120 rpm. The diameter of the coring member 20 is preferably between about 0.1 to about 5 mm and most preferably about 2 mm.

Preferably, the rate of linear advancement of the coring member through tissue is not greater than the rate of cutting of the serrated edge of the coring member. In a preferred embodiment, the maximum cutting rate can be calculated as follows:

Number of serrated teeth 'n'×tooth depth (t)×rpm. For example, a 2.1 mm (O.D.) member having 10 teeth and a tooth depth of 0.147 mm rotating at 120 rpm is preferably advanced at a rate of about 176 mm/min (2.9 mm/sec). Advancing at a rate faster than described above may cause the member edge to longitudinally cut or tear tissue. Such an event decreases the likelihood of obtaining reproducible cores. As far as TMR is concerned, as well as other coring procedures, if some degree of linear cutting or tearing is desirable (i.e., increases the likelihood of the channels remaining open) the degree of linear cutting or tearing can be controlled by the presently disclosed device, i.e., by controllably advancing the coring member at a controlled rate faster than the cutting rate described above. Those skilled in the art will learn by experimentation with the device and particular forms of tissue how to select cutting rate(s) and advancement rate(s) to obtain desired effects on the tissue.

With reference to FIGS. 2, 5 and 9, coring device 10 can include a suction adapter 106 including tubular extension 108 and an outlet port 110. The suction adapter 106 is supported within the housing 12 adjacent the rear end of the cylindrical member 40. A central throughbore (not shown) in tubular extension 108 slidably receives and sealingly engages first end 98 of tubular member 96. First end 98 of tubular member 96 should extend within tubular extension 108 a distance greater than the maximum stroke of coring member 20 to maintain vacuum communication during operation. The outlet port 110 passes through an opening 122 formed in the housing 12, and may be connected to a receptacle 112 by a flexible vacuum line 114. Receptacle 112 is connected to a conventional vacuum source 116. See FIG. 14A.

Coring device 10 can also include a cautery assembly including first and second contacts 116 and 118, respectively, and a dielectric spacer 120 (See FIGS. 3, 5 and 10). First contact 116 includes a cylindrical body 128 that extends through opening 17 in housing 12. The cylindrical body 128 has an annular edge 126 that projects outwardly from opening 17 beyond the outer surface of housing 12. Annular edge 126 can be flat, but is preferably tapered to facilitate contact with body tissue.

Dielectric spacer 120 includes a cylindrical body portion 129 dimensioned to be received within a throughbore formed in first contact 116. The second contact 118 abuts against spacer 120 and is positioned in electrical communication with coring member 20. Terminals 130 and 132 extend through housing 12 and are connected to first and second contacts 116 and 118, respectively, via wires 134 and 136. The terminals 130 and 132 are adapted to be connected to a suitable power source. The power source can provide continuous power to the cautery assembly or provide a series of power pulses. Although shown in a bipolar configuration herein, monopolar configurations are also contemplated.

Referring to FIGS. 9 and 13, in one embodiment, an oscillatory assembly such as ultrasonic generator can be incorporated to impart oscillatory motion to the coring member 20. The ultrasonic generator 119 of this embodiment includes a harmonic element supported between housing half-sections 12a and 12b in engagement with the advancing assembly "Y" of the coring device 10, and can be of the type disclosed in U.S. Pat. No. 5,026,387, issued on Jun. 25, 1991, to Thomas. A mounting structure, such as keyed track (not shown), supports the ultrasonic generator within the housing 12 while permitting the ultrasonic generator 119 to move linearly as coring member 20 is advanced. The ultrasonic generator 119 can be used in conjunction with the advancing and rotation assemblies to oscillate the coring member 20 as the member is rotated and advanced. Oscillation of the coring member can effect frictional cutting and/or cauterization of the tissue. The ultrasonic generator 119 can also be operated solely in conjunction with the advancing assembly at a frequency coordinated with the rate of advancement of the advancing assembly to provide coring of body tissue.

Operation of coring device 10 will now be described with reference to FIG. 13. As discussed above, when motor 22 is actuated, shaft 24 is rotated to rotate worm 26 and bevel gear 28. Bevel gear 28 engages and rotates bevel gear 34 which in turn rotates rod member 36 and compression nut 48. Coring member 20 is fastened to compression nut 48 by flexible washer 50, as illustrated in FIG. 11, such that coring member 20 rotates with compression nut 48.

Worm 26 engages worm gear 60 of the first gear set to rotate worm gear 60, rotatable shaft 62, and gear 58. When movable trigger 16 is acted upon in the direction indicated by arrow "A", to move actuation gear 78 into engagement with rotating gear 58, actuation gear 78 is rotated in the direction indicated by arrow "B". Actuation gear 78 is engaged with gear 68 of the second gear set and rotates gear 68, rotatable shaft 72, and gear 70. Teeth on gear 70 engage teeth on toothed rack 52 to advance toothed rack 52 linearly in the direction indicated by arrow "C". Since toothed rack 52 is fastened to cylindrical member 40 and cylindrical member 40 engages peripheral face 44 of rod member 36, cylindrical member 40 and rod member 36 are also linearly advanced causing corresponding advancement of compression nut 48 and coring member 20 in the direction indicated by arrow "D".

FIG. 13A illustrates a control device to limit the distal advancement of coring member 20. The control device 10 includes first and second motor contacts 134 and 136 which are removably mounted on any of a series of pegs 138 formed within housing half-section 12b to vary the maximum distance of advancement of coring member 20. Each contact 134 and 136 electrically communicates with a corresponding terminal 141 and 143 of motor 22. Contacts 134 and 136 are normally positioned in contact with each other such that when power is supplied to the motor 22 via cable 18, the circuit is complete and motor 22 is turned on. To limit the distal advancement of coring member 20, an annular flange 141 is formed on compression nut 48. As compression nut 48 is advanced a predetermined linear distance in the direction indicated by arrow "E", annular flange 140 engages and deflects contact 136 to interrupt the motor circuit and stop motor 22. A return spring 143 positioned about coring member 20 between cautery contact 116 and compression nut 48 (see FIG. 5) returns the coring member 20 to a retracted position. The return spring will not move the member until trigger 16 is released and the gears providing longitudinal motion are disengaged.

Figure 14:
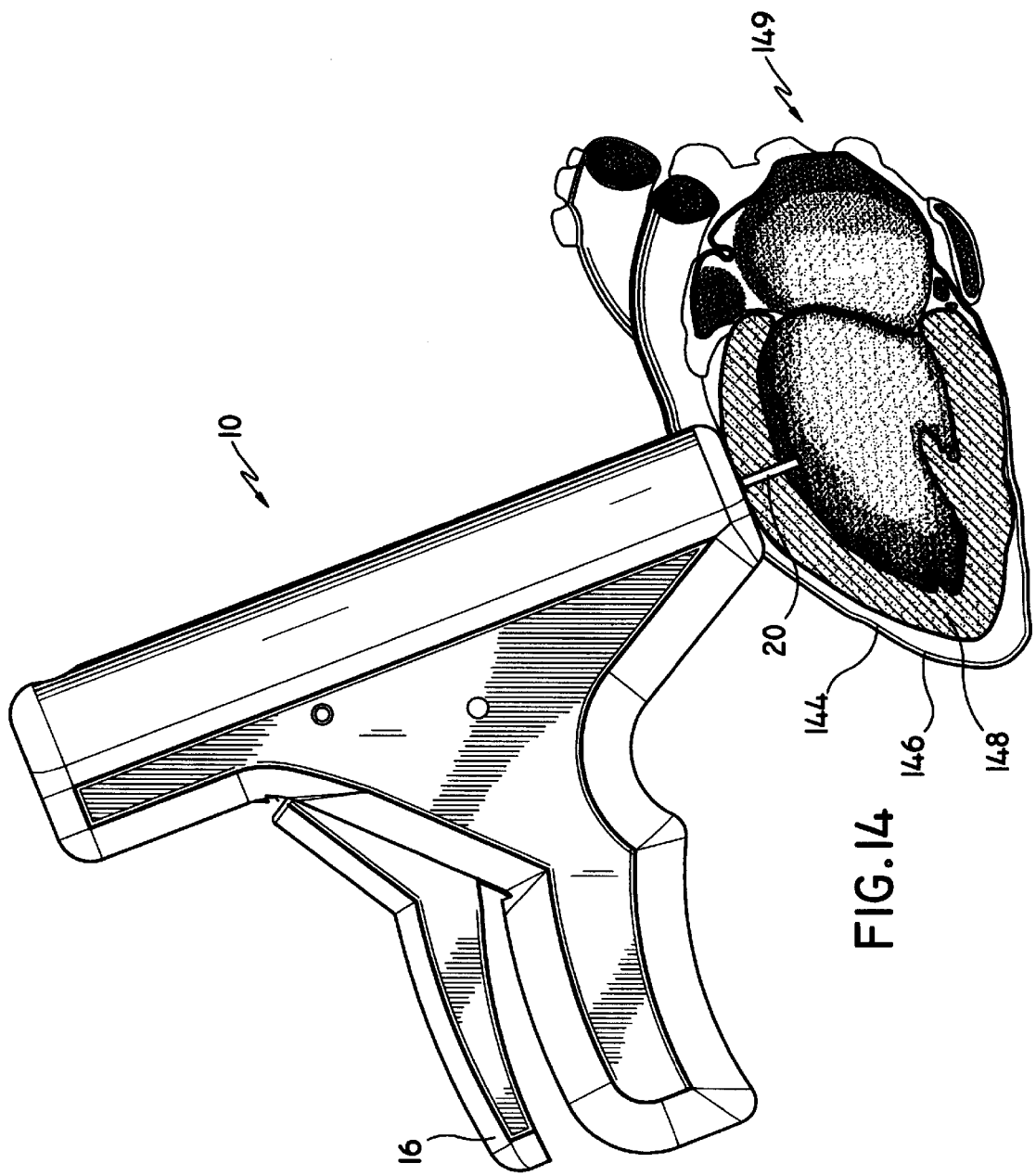
FIG. 14 is a perspective view which illustrates the coring device shown in FIG. 1 in position adjacent body tissue with the coring member in an extended position.

FIG. 14 illustrates coring device 10 during a TMR procedure. The end face of the instrument is placed against the tissue to be cored and motor 22 is operated to rotate coring member 22. In FIG. 14, movable trigger 16 has been acted upon to actuate the linear advancement assembly to advance the coring member 20 from the epicardium 146 through the myocardium 148 and into the left ventricle 144 of the heart 149. During the TMR procedure, 1 or more channels can be cored into the heart to facilitate internal blood delivery to oxygen starved areas of the heart. During or after the coring member has created a hole, thermal energy can be transferred from the member to the tissue by means of, for example, electrocautery or ultrasound. Such energy may affect the ability of the channel to remain open.

Typically, a healthy human heart has a wall thickness of 10–15 mm. A diseased heart can be as thick as 40 mm (measured from the outer surface of the epicardium to the inner wall of the myocardium). The contacts 134 and 136 should be properly positioned on pegs 138 prior to performing the TMR procedure to allow coring member 22 to core through the thickness of the heart being treated, i.e., the coring member should have a stroke length at least as great as the thickness of the heart wall to be perforated. Successful entry into the ventricle can be visually apparent upon the appearance of blood in the vacuum line 114.

Figure 15:
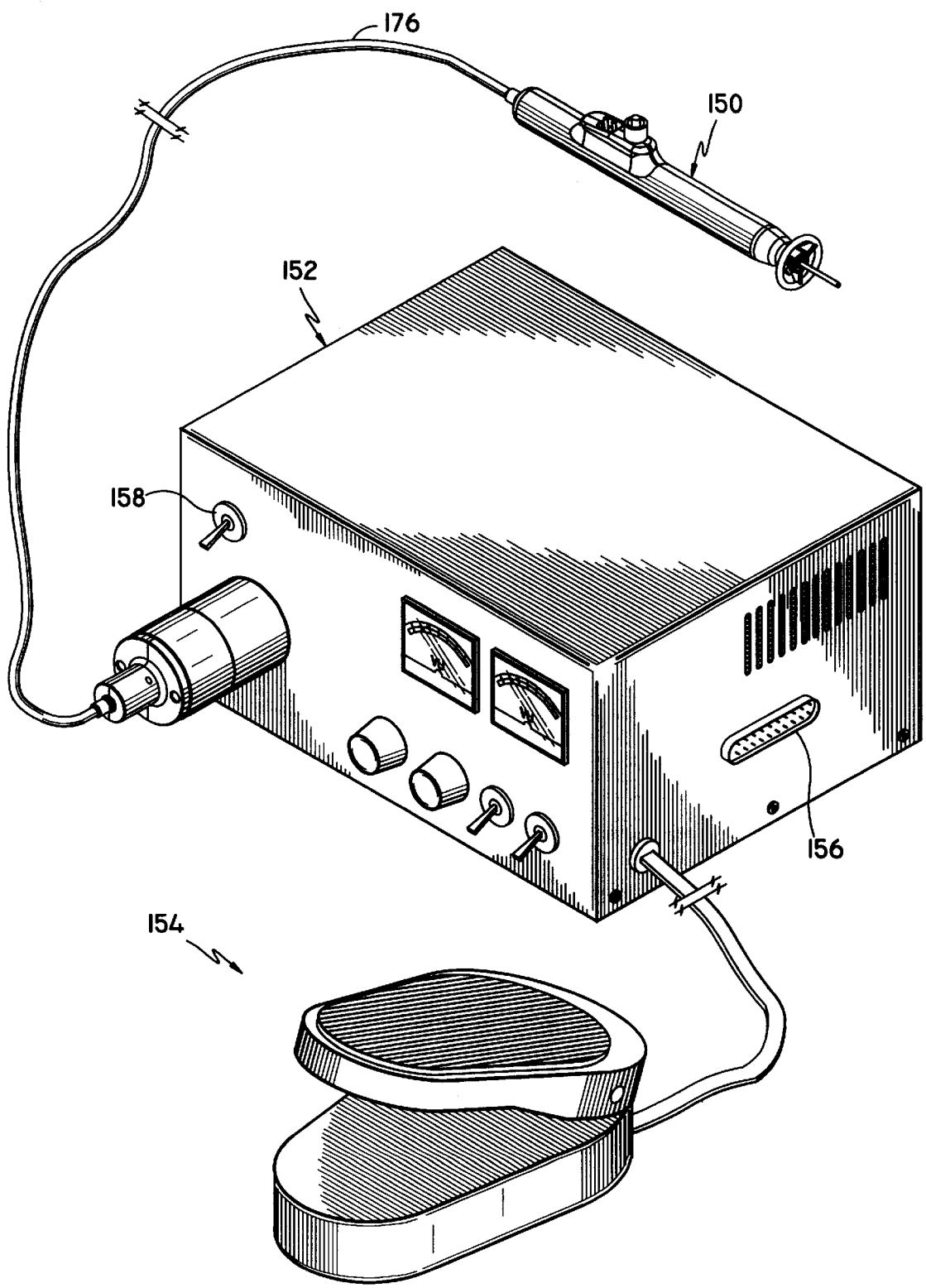
FIG. 15 is a perspective view of another embodiment of the coring device in association with a control assembly.

An alternative embodiment of the presently disclosed coring device will now be described with reference to FIGS. 15–25. FIG. 15 illustrates a coring device 150, and a control assembly including a control module 152 and a foot operated actuator 154 for actuating the control module 152. A flexible shaft 188 (see FIG. 17) wrapped in a shaft casing 176 extends between the control module 152 and the coring device 150. Flexible shaft 188 should be of the type capable of transmitting both rotary and linear motion in the manner similar to a solid steel shaft, and can be of the type commercially available from S.S. White Technologies of Piscataway, N.J. Flexible shaft 188 preferably has multiple layers of wire wrapped around a mandrel, with each layer being formed of multiple strands of wire.

The control module 152 includes dual-motion capability that can provide precise linear and rotary motion to flexible shaft 188. Two stepper motors can provide such motion. Flexible shaft 188 is preferably coupled to the control module 152 and is rotated and advanced within shaft casing 176 and coring device 150. Motion of flexible shaft 188 is translated to the internal components of the coring device 150. A suitable dual-motion unit and the associated circuitry necessary to adapt the unit for use with the coring device 150 of the present disclosure is commercially available through Haydon Switch and Instrument, Inc. of Waterbury, Conn. or Eastern Air Devices, Inc. of Dover, N.H.

Control module 152 further includes a receptacle 156 adapted to engage a terminal of a programmable computer, such that control module 152 can interface with the computer. The software required to program the programmable dual-motion unit is commercially available through Intelligent Motion Systems, Inc. of Taftville, Conn. A toggle switch 158 can be provided to switch the control module 152 from an operation mode to a test mode. In the test mode, when the foot actuator is acted upon, coring member 170 is moved sequentially from a fully retracted position to a fully extended position and back to the fully retracted position. The control module 152 may also have a setting for servicing the coring member 170, such that when actuated, the coring member is extended without rotation to facilitate removal of the coring member 170 from the coring device 150.

Figure 16:
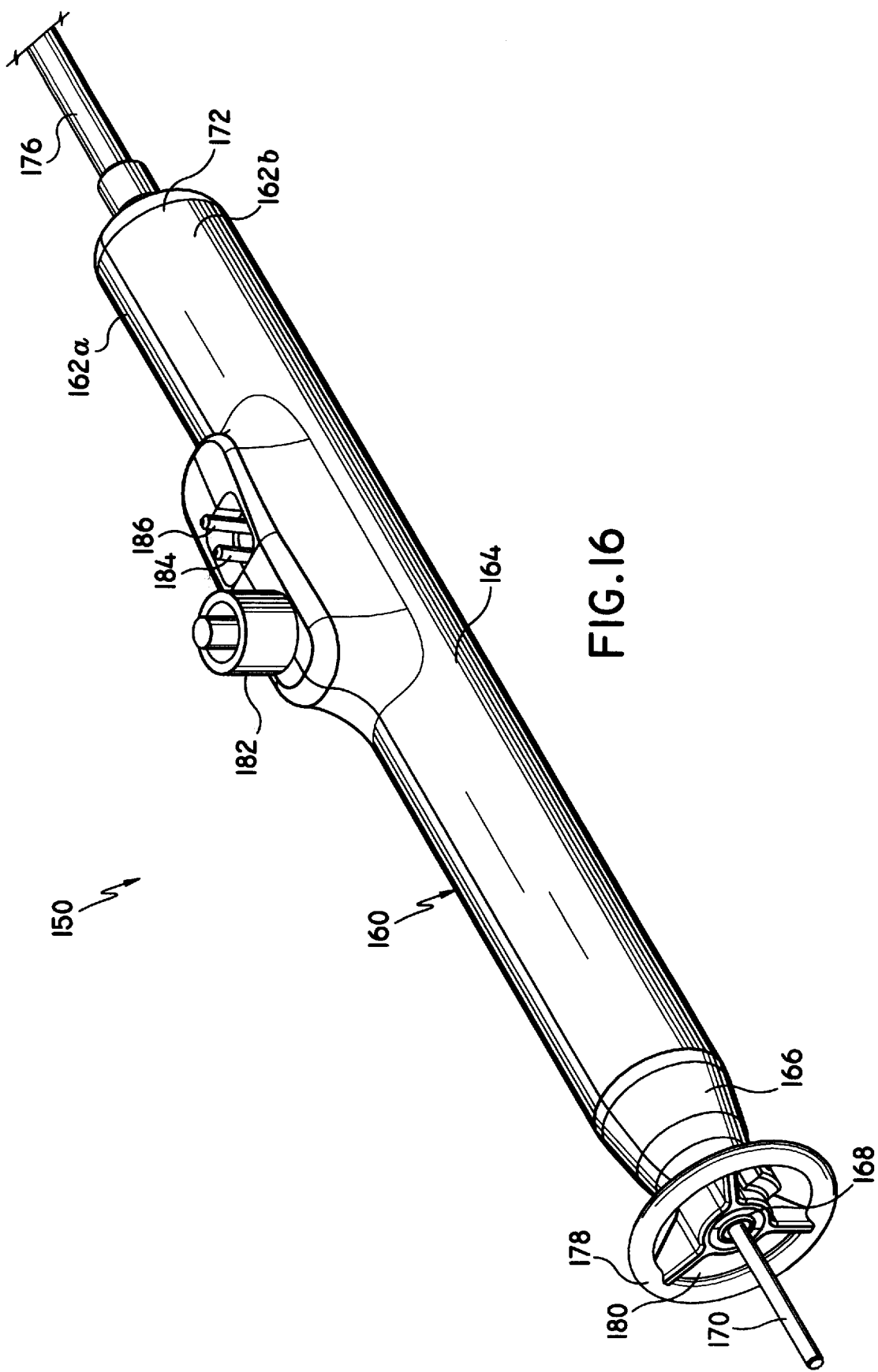
FIG. 16 is a perspective view of the coring device shown in FIG. 15.

FIG. 16 illustrates coring device 150. Briefly, coring device 150 includes a housing 160 formed from molded housing half-sections 162a and 162b. Housing 160 includes an elongated body 164 having a first end 166 with an opening 168 dimensioned to permit reciprocation and rotation of coring member 170, and a second end 172 having an opening dimensioned to receive flexible shaft 188. A locator ring 178 having viewing ports 180 can be integrally formed with, or removably attached to, the first end 166 of body 164. A locking screw can be used to removably secure locator ring 178 to body 164. The locator ring 178 is positioned about opening 168 and coring member 170 and can be positioned in engagement with the epicardial wall of the heart during a TMR procedure to help to properly orient the device with the heart. A suction adapter 182 and cautery terminals 184 and 186 can be provided and positioned to extend through ports formed in housing 160.

Figure 17:
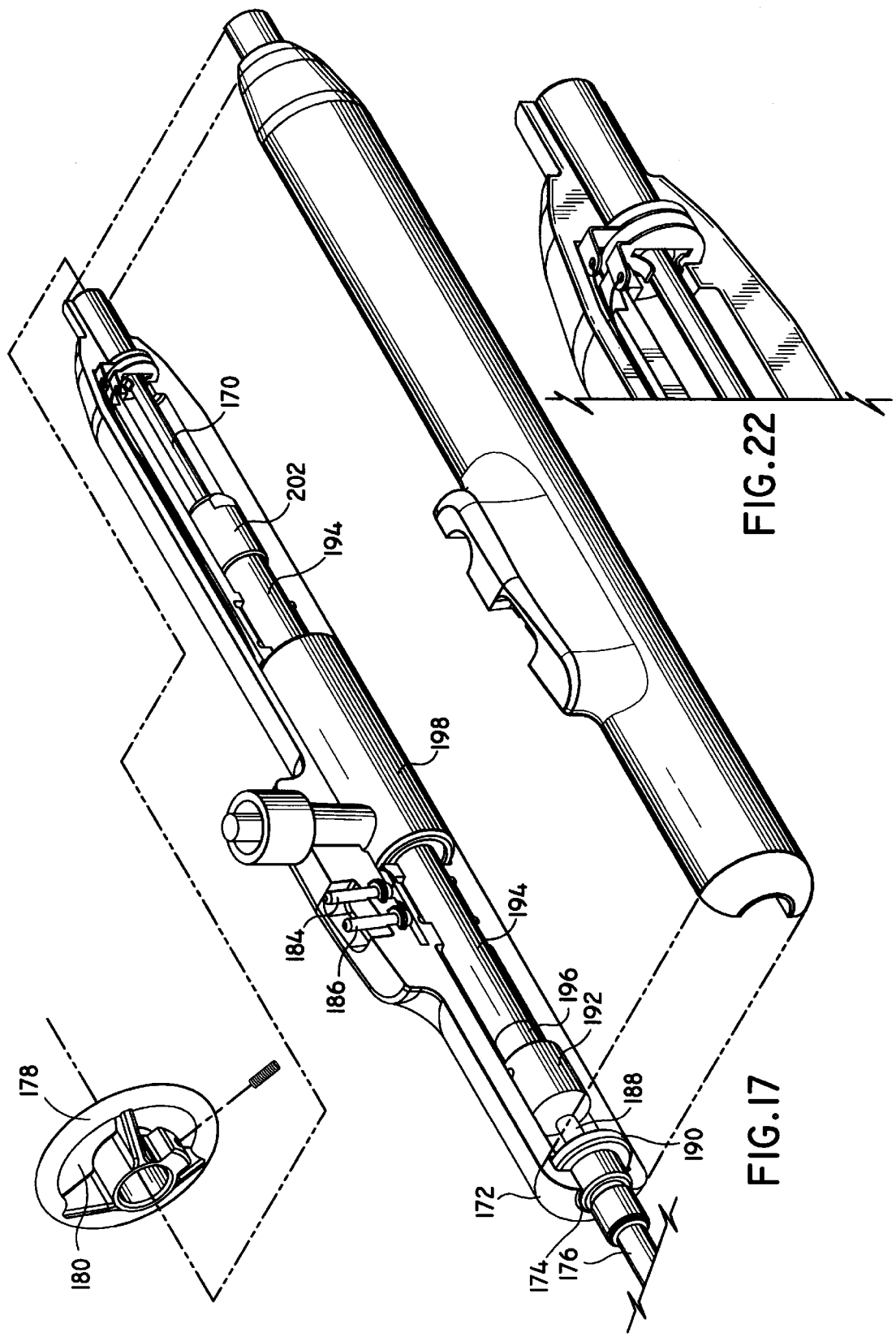
FIG. 17 is a perspective view with parts partially separated of the coring device shown in FIG. 15.
Figure 18:
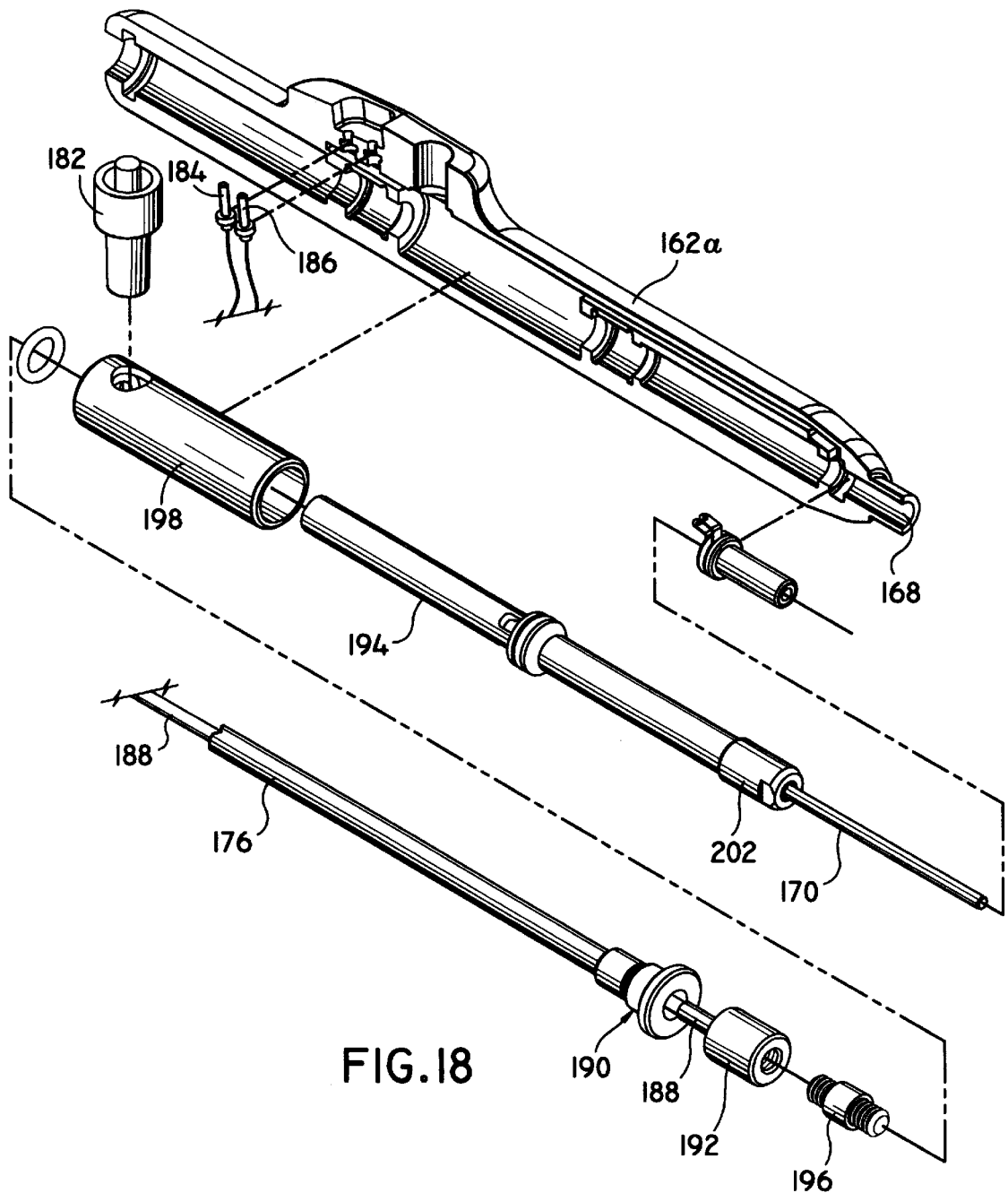
FIG. 18 is a perspective view with parts separated of the coring device shown in FIG. 15.

Referring to FIGS. 17 and 18, flexible shaft 188 extends from control module 152 through shaft casing 176 and a swivel assembly 190 into the housing 160. The end of the flexible shaft 188 positioned within the housing 160 is fastened to a linearly movable, rotatable piston 192. Piston 192 is connected to an elongated shaft 194 via a threaded connector 196. Elongated shaft 194 extends distally through a suction chamber 198 and is connected at its distal end to a member adapter 200 (FIG. 19) by clamping nut 202. Coring member 170 is removably secured within member adapter 200 by the clamping nut 202. The flexible shaft 188, piston 192, connector 196, elongated shaft 194, member adapter 200, and member 170 are fastened together to translate rotary and linear motion of shaft 188 to corresponding motion of the components listed above.

Figure 19:
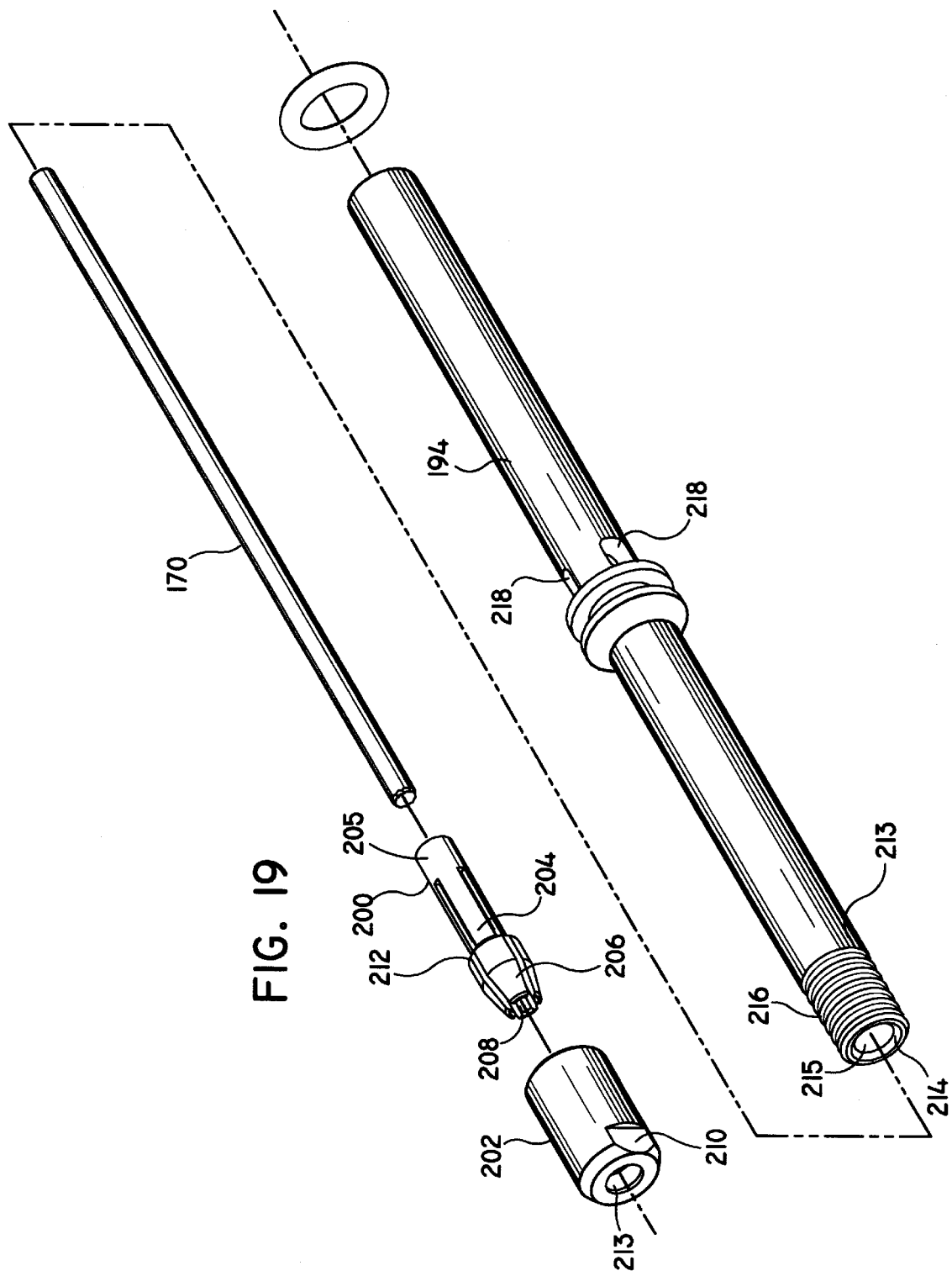
FIG. 19 is a perspective view with parts separated illustrating the clamping nut, the member adapter, the elongated shaft, and the coring member of the coring device shown in FIG. 15.

Referring to FIG. 19, member adapter 200 preferably includes a plurality of annularly positioned flexible legs 204 which extend longitudinally from a cylindrical base portion 205. Each leg 204 is formed with an increased diameter portion 212 and a tapered cam surface 206. The member adapter 200 defines a central throughbore 208 having an internal diameter greater than the outer diameter of the coring member 170. Coring member 170 extends through central bore 208 of member adapter 200 and through a partially threaded throughbore 213 formed in clamping nut 202.

As illustrated in FIGS. 20 and 21, the elongated shaft 194 has a threaded end 216 dimensioned to engage partially threaded throughbore 213 of clamping nut 202. With coring member 170 extending through member adapter 200 and clamping nut 202 and with the member adapter 200 positioned in throughbore 213 of clamping nut 202, clamping nut 202 is threadingly engaged to threaded end 216 of elongated shaft 194 to deflect flexible legs 204 into clamping engagement with coring member 170.

Coring device 150 can include a suction assembly to remove the cored tissue from the surgical site. The suction assembly includes suction adapter 182 and suction chamber 198. Suction chamber 198 is fixedly positioned in a recess formed in housing half-sections 162a and 162b. The first end of suction chamber 198 is formed with a bore 220 having substantially the same internal dimensions as the outer surface of elongated shaft 194. A flexible ring seal 222 is positioned in a recess formed in the first end of the suction chamber 198 to seal the area between the elongated shaft 194 and the bore 220 while permitting the elongated shaft 194 to slide through the bore 220. The elongated shaft 194 includes a pair of annular flanges 224 which define a seal recess 226. Flexible seal 228 is positioned within seal recess 226 and engages the internal walls of suction chamber 198 as the elongated shaft 194 is reciprocated therethrough to define a sealed compartment 230.

Elongated shaft 194 is provided with a central bore 232 that extends from threaded end 216 of shaft 194 to a series of circumferentially aligned ports 234 formed in shaft 194. Ports 234 communicate with sealed compartment 230. Coring member 170 has a central bore 236 in communication with central bore 232 of elongated shaft 194. Cored tissue entering the distal end of coring member 170 can travel through member 170, into bore 232 of shaft 194, through ports 234, and into sealed compartment 230.

Figure 14A:
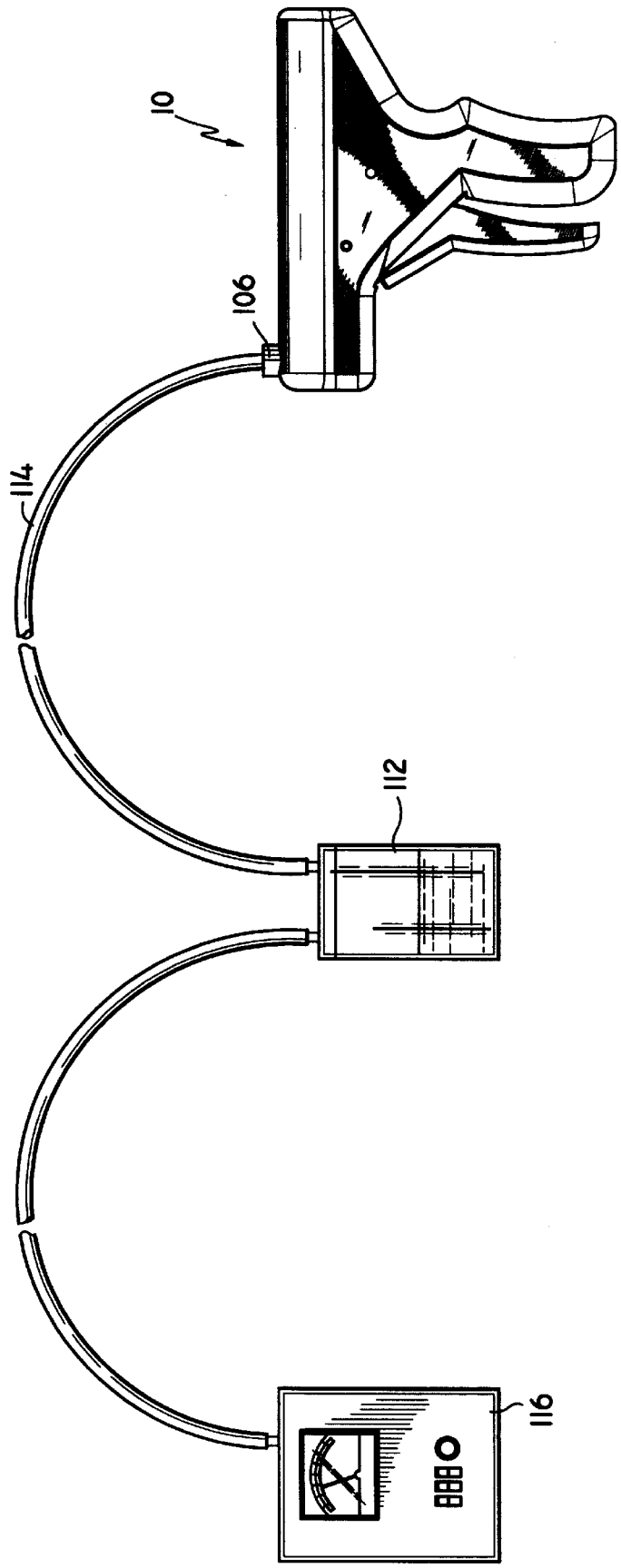
FIG. 14A is a side view of a biopsy retrieval assembly connected to the coring device shown in FIG. 1.

Suction adapter 182 has a central bore that communicates with sealed compartment 230 and an outlet port 238. As illustrated in FIG. 14A with respect to device 10, outlet port 238 may be similarly connected to a receptacle 112 by a flexible tube 114. Receptacle 112 is connected to a conventional vacuum source 116.

Figure 23:
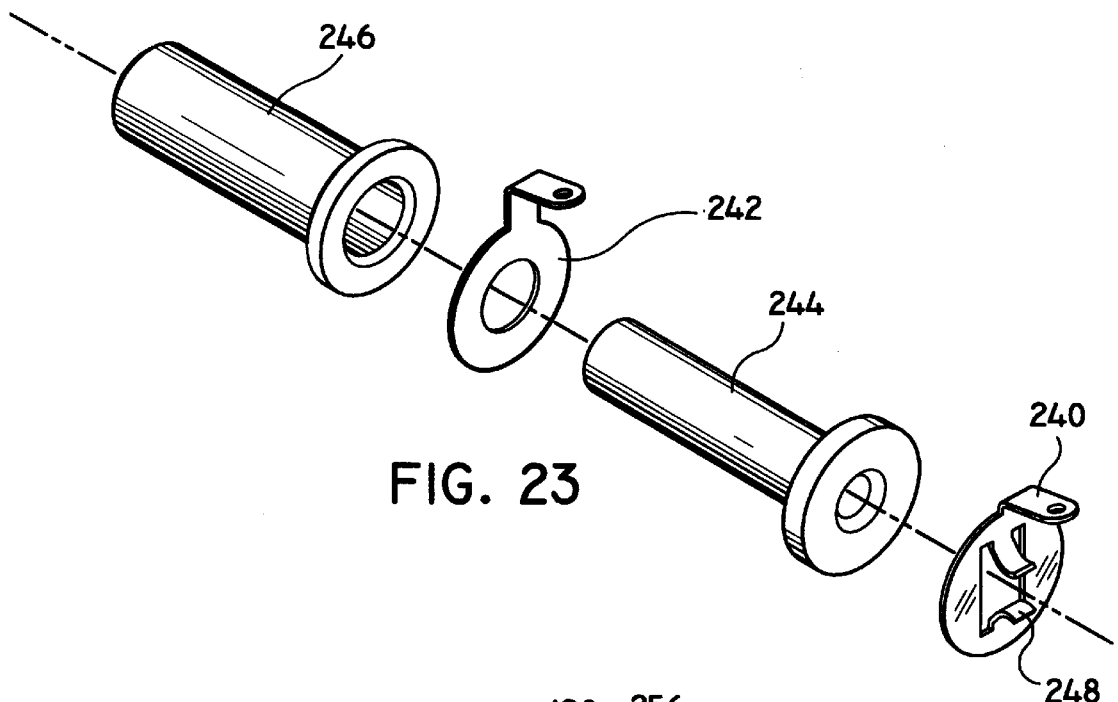
FIG. 23 is a perspective view with parts separated of the cautery assembly of the coring device shown in FIG. 15.

FIGS. 21–23 illustrate a cautery assembly which can be incorporated into coring device 170. The cautery assembly includes first and second contacts 240 and 242, a cylindrical dielectric spacer 244 and a conductive cylindrical member 246. First contact 240 has a pair of flexible tabs 248 that engage coring member 170 that is constructed from an electrically conductive material. Second contact 242 engages cylindrical member 246, and is separated from first contact 240 by dielectric spacer 244. Cylindrical member 246 extends through opening 174 and is positioned about coring member 170, and includes an annular edge 250 that projects outwardly from opening 174. Annular edge 250 can be flat, but is preferably tapered to enhance contact with body tissue. Dielectric spacer 244 is positioned between coring member 170 and cylindrical member 246 to prevent arcing between the two members.

First and second contacts 240 and 242 are electrically connected to cautery terminals 184 and 186 by wires 252 and 254. Terminals 184 and 186 are adapted to be connected to a suitable power source. Power can be supplied to the cautery assembly continuously during the coring procedure or supplied in timed pulses.

Figure 24:
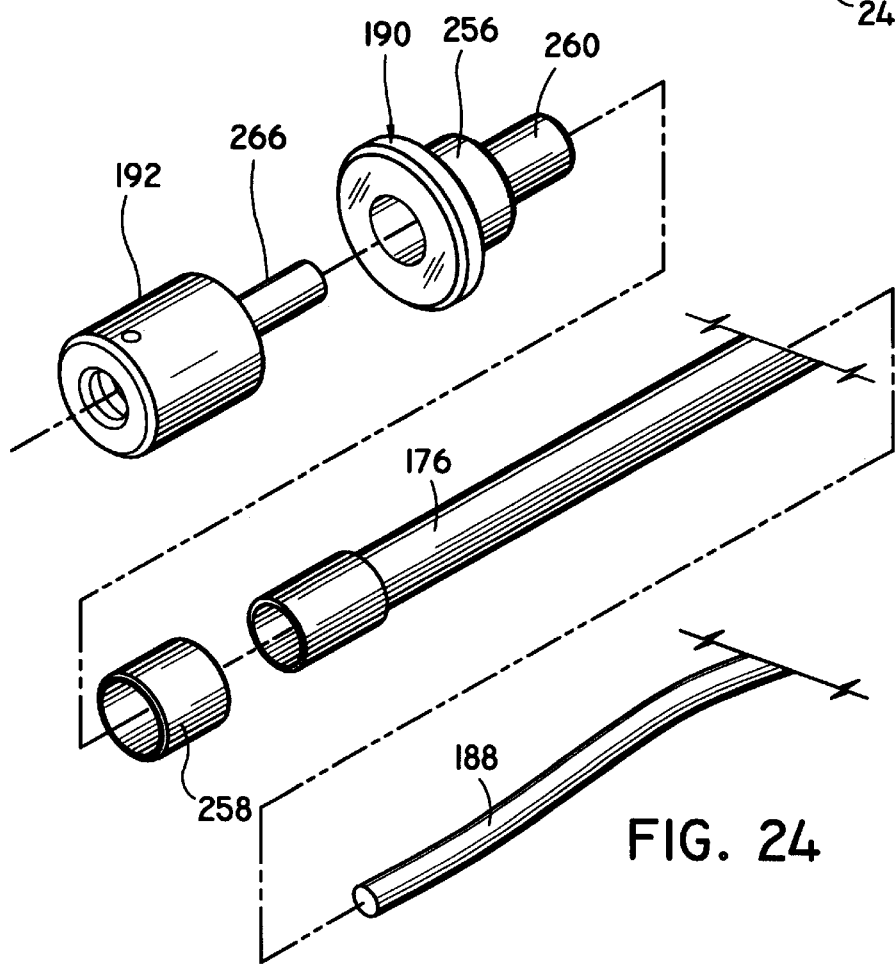
FIG. 24 is a perspective view with parts separated of the swivel assembly and its adjacent components of the coring device shown in FIG. 15.

Referring now to FIG. 24, a swivel assembly 190 is positioned at the second end of housing 172. Swivel assembly 190 includes a swivel coupling 256 rotatably positioned within an annular recess formed in housing half-sections 162a and 162b. The swivel coupling 256 has a cylindrical extension 260 about which casing 176 extends. Annular clamp 258 is positioned about extension 260 and casing 176 to secure casing 176 to swivel coupling 256. Flexible shaft 188 extends through swivel coupling 256 and is crimped within a rearwardly extending portion 266 of piston 192. See FIG. 20. Coring device housing 160 is rotatable about swivel coupling 256 independently of the internal components of the device 150.

Figure 25:
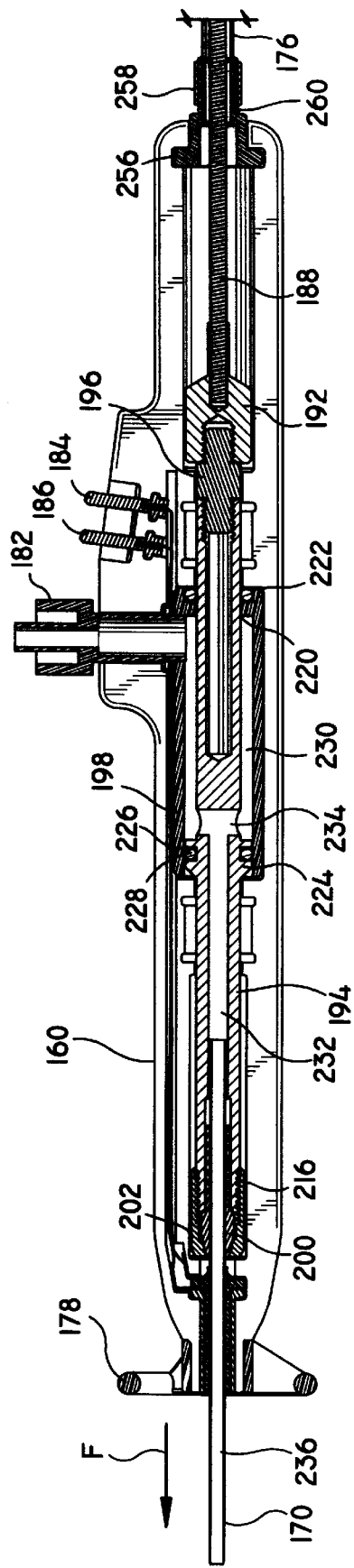
FIG. 25 is a side cross-sectional view of the coring device shown in FIG. 15 with the coring member in an extended position.

Referring now to FIG. 25, when control module 152 is actuated to provide linear and rotary motion to flexible shaft 188, this motion is translated to piston 192, connector 196, elongated shaft 194, member adapter 200, and clamping nut 202 to linearly advance and rotate coring member 170 in the direction indicated by arrow "F". Control module 152 can be programmed to provide either rotation of shaft 188 in one direction or oscillatory rotation of shaft 188. It is noted that the distal end of coring member 170 can be identical to coring member 20 and will not be discussed in detail. Similarly, the preferred rates of advancement and rotation for performing a TMR procedure can be identical to those disclosed with respect to coring device 10 and will not be discussed in detail.

It will be understood that various modifications can be made to the embodiments disclosed herein. For example, while specific preferred embodiments of driving, advancing, rotating, cauterizing and oscillation assemblies, have been described in detail, structures that perform substantially the same function in substantially the same way to achieve substantially the same result can also be used. Also, while electrical motors have been specifically disclosed herein, air, pneumatic, hydraulic or other types of motors can be used to advance and/or rotate the coring device. In addition, the cautery assemblies can include monopolar circuitry rather than bipolar circuitry as disclosed. Also, besides TMR, the coring device can be used to perform human and veterinary surgical procedures including biopsy retrieval, bone marrow retrieval and other similar procedures. Body tissue other than heart tissue can be cored including liver tissue, bone tissue, skin tissue, etc. Also, depending on the type of tissue and procedure, the coring tool need not be hollow throughout the entire length and can be closed at the proximal end. Therefore, the above description should not be construed as limiting, but merely as exemplifications of preferred embodiments. Those skilled in the art will envision other modifications within the scope and spirit of the claims appended thereto.

What is claimed is:

1. A coring device comprising:
   a housing defining a longitudinal axis;
   a coring member mounted in said housing;
   an advancing assembly mounted for engagement with said coring member to effect longitudinal motion thereof;
   a drive assembly connected to said advancing assembly for activating said advancing assembly to move the coring member longitudinally at a predetermined rate to core body tissue; and
   an electrical element connected to said coring member to provide cauterizing current to body tissue.

2. A coring device according to claim 1, further comprising a rotation assembly mounted for engagement with said coring member, said drive assembly connected to said rotation assembly for activating said rotation assembly to rotate the coring member in coordination with the longitudinal advancement of the coring member.

3. A coring device according to claim 1, further comprising an oscillation assembly mounted for engagement with said coring member, said oscillation assembly effecting oscillation of the coring member.

4. A coring device according to claim 3, wherein said oscillation assembly comprises an ultrasonic generator connected to the coring member.

5. A coring device comprising:
   a coring member;
   a rotation assembly operably connected to the coring member;
   an advancing assembly operably connected to the coring member;
   a drive assembly operably connected to the rotation assembly and advancing assembly, the drive assembly being operable to activate the rotation and advancing assembly to rotate and advance the coring member at predetermined coordinated rates to effect coring of body tissue; and
   a control module, the control module including the drive assembly and being programmable to coordinate the rates of advancement and rotation of the coring member.

6. A coring device according to claim 5, wherein the coring member, the rotation assembly, the advancing assembly, and the drive assembly are supported within a single housing.

7. A coring device according to claim 6, further comprising a movable trigger, and wherein the advancing assembly includes an actuation gear actuated by the movable trigger, the movable trigger being selectively movable to operably connect the advancing assembly to the drive assembly to advance the coring member.

8. A coring device according to claim 7, further comprising an ultrasonic assembly operably connected to the coring member to oscillate the coring member.

9. A coring device according to claim 8, wherein the coring member is oscillated along its longitudinal axis.

10. A coring device according to claim 5, further comprising a cautery assembly operably connected to the coring member.

11. A coring device according to claim 5, wherein the drive assembly includes first and second stepper motors, the first stepper motor being operably connected to the advancing assembly and the second stepper motor being operably connected to the rotation assembly.

12. A coring device according to claim 11, further comprising a flexible shaft extending from the control module to the coring member, wherein said flexible shaft translates linear and rotary motion from the drive assembly to the coring member.

13. A coring device comprising:
    a coring member;
    a longitudinal oscillatory assembly operably connected to the coring member;
    an advancing assembly operably connected to the coring member; and
    a drive assembly operably connected to the oscillatory assembly and the advancing assembly, the drive assembly being operable to advance the coring member at predetermined coordinated rates to effect coring of body tissue while controlling the degree of tearing of the body tissue, wherein the drive assembly includes an electric motor and a harmonic generator, the electric motor being operably connected to the advancing assembly and the harmonic generator being operably connected to the oscillatory assembly.

14. A coring device comprising:

a coring member;

a rotation assembly operably connected to the coring member;

an advancing assembly operably connected to the coring member; and a drive assembly operably connected to the rotation assembly and to the advancing assembly, the drive assembly being operable to activate the rotation and advancing assemblies to rotate and advance the coring member at predetermined coordinated rates to effect coring of body tissue, wherein during advancement of the coring member, the coring member is rotated at least one revolution.

15. A coring device comprising:

a coring member;

a longitudinal oscillatory assembly operably connected to the coring member;

an advancing assembly operably connected to the coring member; and a drive assembly operably connected to the oscillatory assembly and the advancing assembly, the drive assembly being operable to simultaneously advance and oscillate the coring member at predetermined coordinated rates to effect coring of body tissue while controlling the degree of tearing of the body tissue.

16. A method of coring body tissue comprising the steps of:

(a) providing a coring device having a linearly advanceable, rotatable coring member;

(b) positioning the coring device adjacent to the body tissue to be cored;

(c) simultaneously advancing and rotating the coring member at predetermined coordinated rates to core the body tissue; and (d) cauterizing the cored body tissue.

17. A method according to claim 16, wherein the predetermined rate of rotation is from about 1 to about 3000 rpm.

18. A method of according to claim 17, wherein the predetermined rate of rotation is between about 100 to about 140 rpm.

19. A method according to claim 18, predetermined rate of rotation is between about 120 rpm.

20. A method according to claim 16, wherein the predetermined rate of advancement is between about 0.1 to about 50 mm/sec.

21. A method according to claim 20, wherein the predetermined rate of advancement is between about 2 to about 4 mm/sec.

22. A method according to claim 21, wherein the predetermined rate of advancement is about 3 mm/sec.

23. A method according to claim 16, wherein the body tissue is selected from the group consisting of heart tissue, liver tissue, brain tissue, skin tissue, and bone tissue.

24. A method according to claim 16, further including the step of:

(d) simultaneously oscillating the coring member along the longitudinal axis of the coring member.

25. A method of coring body tissue comprising the steps of:

(a) providing a coring device having a linearly advanceable coring member;

(b) positioning the coring member adjacent body tissue;

(c) advancing the coring member into the body tissue at a controlled, constant rate; and (d) withdrawing a portion of the body tissue through at least a portion of the coring member.

26. The method according to claim 25, further comprising the step of rotating the coring member during the step of advancing the coring member.

27. The method according to claim 25, further comprising the step of ultrasonically vibrating oscillating the coring member during the step of advancing the coring member.

28. The method according to claim 25, further comprising the step of applying cauterizing energy to the coring member while the coring member is in contact with the body tissue.

29. The method according to claim 25, further comprising the steps of providing a vacuum source and operably connecting the vacuum source to the coring member.

30. The method according to claim 25, wherein the step of advancing the coring member comprises actuating a controlling device to control the step of advancing.

31. The method according to claim 30, further comprising the step of providing a length of cable having first and second ends, the cable first end being operably connected to the controlling device and the cable second end being operably connected to the coring device.

32. A method of performing transmyocardial revascularization comprising the steps of:

(a) providing a coring device having a linearly advanceable coring member;

(b) positioning the coring member adjacent heart tissue;

(c) advancing the coring member into the heart tissue at a controlled, constant rate.

33. A method of coring body tissue comprising the steps of:

(a) providing a coring device having a linearly advanceable coring member;

(b) providing a device for delivering a ultrasonic energy to the coring member;

(c) positioning the coring member adjacent body tissue;

(d) advancing the coring member into the body tissue; and (e) delivering ultrasonic energy to the coring member at a time when the coring member is in contact with the body tissue.

34. A method of coring body tissue comprising the steps of:

(a) providing a coring member having 'n' serrations at an end thereof, each serration have a tooth depth 't';

(b) rotating the coring member at a rate 'r'; and (c) linearly advancing the coring member at a rate less than or equal to the product of 'n', 't' and 'r'.

35. The method according to claim 34, wherein the coring member is advanced at a constant rate.

36. The method according to claim 34, wherein the coring member is rotated at a constant rate.

37. A method of coring body tissue comprising the steps of:

(a) providing a coring device having linearly advanceable, rotatable coring member;

(b) positioning the coring device adjacent to the body tissue to be cored; and (c) simultaneously advancing and rotating the coring member at predetermined coordinated rates to core the body tissue, wherein during continuous advancement of the coring member, the coring member is rotated at least one revolution.

* * * * *